US010202451B2

(12) United States Patent
Konopitzky et al.

(10) Patent No.: US 10,202,451 B2
(45) Date of Patent: Feb. 12, 2019

(54) CD33 BINDING AGENTS

(71) Applicant: Boehringer Ingelheim International GmbH, Ingelheim am Rhein (DE)

(72) Inventors: Renate Konopitzky, Bad Voeslau (AT); Eric Borges, Moedling (AT); Paul Adam, Vienna (AT); Karl-Heinz Heider, Stockerau (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/375,313

(22) Filed: Dec. 12, 2016

(65) Prior Publication Data
US 2017/0088617 A1  Mar. 30, 2017

Related U.S. Application Data

(62) Division of application No. 14/742,836, filed on Jun. 18, 2015, now Pat. No. 9,550,833, which is a division of application No. 13/246,022, filed on Sep. 27, 2011, now Pat. No. 9,079,958.

(30) Foreign Application Priority Data

Oct. 4, 2010  (EP) ..................................... 10186468

(51) Int. Cl.
*A61K 39/395* (2006.01)
*C07K 16/28* (2006.01)

(52) U.S. Cl.
CPC ...... *C07K 16/2803* (2013.01); *C07K 16/2851* (2013.01); *C07K 2317/21* (2013.01); *C07K 2317/34* (2013.01); *C07K 2317/51* (2013.01); *C07K 2317/56* (2013.01); *C07K 2317/565* (2013.01); *C07K 2317/732* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 5,773,001 A | 6/1998 | Hamann et al. |
| 8,124,731 B2 | 2/2012 | Lazar et al. |
| 9,550,833 B2 | 1/2017 | Konopitzky et al. |

FOREIGN PATENT DOCUMENTS

| EP | 138572 A2 | 4/1985 |
| WO | 199320848 | 10/1993 |
| WO | 2004043344 A2 | 5/2004 |
| WO | 2006019447 A1 | 2/2006 |
| WO | 2008058021 A2 | 5/2008 |
| WO | 2008119565 A2 | 10/2008 |
| WO | 2008119567 A2 | 10/2008 |
| WO | 2009019312 A2 | 2/2009 |
| WO | 2010037835 A2 | 4/2010 |
| WO | 2010037836 A2 | 4/2010 |
| WO | 2010037838 A2 | 4/2010 |
| WO | 2011119661 A1 | 9/2011 |
| WO | 2011138391 A1 | 11/2011 |
| WO | 2014029752 A1 | 2/2014 |

OTHER PUBLICATIONS

Amadori, Sergio et al. "Integration of monoclonal antibodies and immunoconjugates into the treatment of acute myeloid leukemia" (2008) Current Opinion in Hematology vol. 15, pp. 95-100.
Caron, et al., "Biological and Immunological Features of Humanized M195 Monoclonal Antibodies", Cancer Research, 1992, p. 6761-6767.
Caron, et al., "Engineered and Humanized Dimeric Forms of IgG sre More Effective Antibodies", Experimental Medicine, Rockefeller Univ Press, 1992.
Caron, et al., American Cancer Society, vol. 73, No. 3, "Murine and Humanized Constricts of Monoclonal Antibody M195 for the Therapy of Acute Myelogenous Leukemia", 1994.
Carter, et al., "Potent Antibody therapeutics by design", Nature Reviews Immunology, 2006, 6, p. 343-357.
Co, Man Sung, et al. "Chimeric and Humanized Antibodies with Specificity for the CD33 Antigen" Journal of Immunology, (1992) vol. 148, 1149-1154.
Hammann, et al., "Gemtuzumab Ozogamicin, a potent and selective Anti-CD33 Antibody-Calicheamicin Conjugate for treatment of Acute Myeloid Leukemia", Bioconjugate Chem., 2002, vol. 13, p. 47-58.
International Search Report and Written Opinion, dated Jan. 30, 2012, for PCT/EP2011069339.
Jahnichen, Sven et al. CXCR4 nanobodies (VHH-based single variable domains) potently inhibit chemotaxis and HIV-1 replication and mobilize stem cells PNAS, (2010) vol. 107, No. 47, pp. 20565-20570.
Joiner, Danese M. et al. "Lrp5 and Lrp6 in Development and Disease" (2013) Trends Endocrinology and Metabolism, vol. 24(1), pp. 31-39.
Korver, et al., "Monoclonal antibodies against IREM-1: potential for targeted therapy of AML", Leukemia, 2009.
Kuegler, et al., "A recombinant trispecific single-chain Fv derivative directed against CD123 and CD33 mediates effective elimination of acute myeloid leukemia cells by dual targeting" ,British Journal of Hematology, 2010, p. 574-586.
Lazar, et al., "Engineered antibody Fc variants with enhanced effector function", PNAS, 2006, vol. 103, No. 11.p. 4005-4010.

(Continued)

*Primary Examiner* — Julie Wu
*Assistant Examiner* — Meera Natarajan
(74) *Attorney, Agent, or Firm* — Atabak R. Royaee

(57) ABSTRACT

The present invention relates to immunotherapies that are based on myeloid cell depletion. In particular, the present invention relates to CD33 binding agents for use in such therapies, e.g. in the treatment of myeloid cell malignancies and myelodysplastic syndrome (MDS).

12 Claims, 5 Drawing Sheets
Specification includes a Sequence Listing.

(56) References Cited

OTHER PUBLICATIONS

Linenburger, et al., "Antibody-directed therapies for hematological malignancies", Journal of Immunotherapy, vol. 8, No. 2, 2002.

Luqman et al., "The antileukemic activity of human anti-CD-40 antagonist antibody, HCD122, on human lymphocytic leukemia cells", Blood, 2008, vol. 112, No. 3, p. 711-720.

Rudnick, et al., "Affinity and Avidity in Antibody-Based Tumor Targeting", Cancer Biotherapy and Radiopharmaceuticals, 2009, vol. 24, No. 2, p. 155-160.

Singer, et al., "Effective Elimination of Acute Myeloid Leukemic Cells by Recombinant Bispecific Antibody Derivatives-Directed Against CD33 and CD16", Journal of Immunotherapy, 2010.

Sutherland, et al., "Anti-leukemic activity of lintuzumab in preclinical models of acute myeloid leukemia", Mabs, 2009, vol. 1, No. 5, p. 481-490.

Tong, et al., Blood, "A non-Internalizing Anti-CD-40 Antibody, CHIR-12.12, Blocks CD40L-Induces Cytokine Production and Mediates Greater ADCC Than Rituximab in Primary CLL Cells," 2014.

Comparison of Sequence Opposed patent WO2012045752. EPO, Notice of Opposition EP 11764553.1 / 2625201, dated Jun. 12, 2017, 4 pgs.

European Patent Office—Notice of Opposition dated Jun. 12, 2017. EP Application No. 11764553.1; Patent No. 2625201.; 01 (Ablynx N.V.) filed Jun. 7, 2017.

European Patent Office—Notice of Opposition dated Jun. 12, 2017. EP Application No. 11764553.1; Patent No. 2625201.; 02 (Strawman Limited) filed Jun. 7, 2017.

Ferlazzo, Guido et al. "Engagement of CD33 surface molecules prevents the generation of dendritic cells from both monocytes and CD34 myeloid precursors" (2000) Eur. J. Immunol. vol. 30, 827-833.

Hoofnagle, Andrew N. et al. "Protein Analysis by Hydrogen Exchange Mass Spectrometry" (2003) Annu. Rev. Biophys. Biomol. Struct., vol. 32, 1-25.

Perez-Oliva, Ana B. et al. "Epitope mapping, expression and post-translational modifications of two isoforms of CD33 (CD33M and CD33m) on lymphoid and myeloid human cells" (2011) Glycobiology, vol. 21, No. 6, 757-770.

Report of experiments carried out by Opponent (Strawman Limited), filed on Jun. 7, 2017. EPO, Notice of Opposition, EP 11764553.1 / 2625201, 5 pgs.

Sequence Listing, WO2008119565 filed Apr. 3, 2008. Micromet AG published by WIPO Oct. 9, 2008.

Sequence table WO2008119567 filed Apr. 3, 2008. Micromet AG, published by WIPO Oct. 9, 2008.

Technical Report provided by Opponent (Ablynx, N.V.), EPO, Notice of Opposition, filed on Jun. 7, 2017. EP 11764553.1 / 2625201; 6 pgs.

U.S. Appl. No. 14/742,836. Excerpt from prosecution. Inventor: R. Konopitzky, filed Jun. 18, 2015. Response to Examiner initated interview filed on Jun. 23, 2016.

U.S. Pat. No. 9,550,833. Granted Claims. Inventor: R. Konopitzky et al., Date of Grant: Jan. 24, 2017. EPO, Notice of Opposition EP 11764553.1 / 2625201, mailed on Jun. 12, 2017. 1 pg.

Van Der Velden, Vincent H.J. et al. "Targeting of the CD33-calicheamicin immunoconjugate Mylotarg (CMA-676) in acute myeloid leukemia: in vivo and in vitro saturation and internalization by leukemic and normal myeloid cells" (2001) Blood, vol. 97, No. 10, 3197-3204.

Kim, Sang Jick et al. "Antibody Engineering for the Development of Therapeutic Antibodies" (2005) Molecules and Cells, vol. 20, No. 1 17-29.

Linenberger, ML "CD33-directed therapy with gemtuzumab ozogamicin in acute myeloid leukemia: progress in understanding cytotoxicity and potential mechanisms of drug resistance" (2005) Leukemia, 19, 176-182.

CD33 BINDING AGENTS

RELATED APPLICATIONS

This application is a divisional of co-pending U.S. application Ser. No. 14/742,836, filed Jun. 18, 2015, which is a divisional of U.S. application Ser. No. 13/246,022, filed Sep. 27, 2011, now U.S. Pat. No. 9,079,958, which claims priority to European application no. 10186468.4, filed Oct. 4, 2010, the contents of which are hereby incorporated herein by reference.

SEQUENCE LISTING

The instant application contains a Sequence Listing which has been submitted in ASCII format via EFS-Web and is hereby incorporated by reference in its entirety. Said ASCII copy is named Sequence Listing 12-0321-US-3-Sequence-Listing.txt and is 125,679 bytes in size.

FIELD OF THE INVENTION

The present invention relates to immunotherapies that are based on myeloid cell depletion. In particular, the present invention relates to CD33 binding agents for use in such therapies, e.g. in the treatment of myeloid cell malignancies and myelodysplastic syndrome (MDS).

BACKGROUND OF THE INVENTION

In the early 1980s CD33 was identified as a marker of myeloid leukemias (Andrews et al., Blood 62, 24-132, 1983). CD33 is a cell-surface antigen specifically expressed on myeloid cells including myeloid leukemia cells. It is the smallest member of the siglec (sialic acid-binding Ig-related lectins) family. CD33 is expressed on early multilineage hematopoietic progenitor cells and myelomonocytic precursors. It is absent from pluripotent hematopoietic stem cells (Andrews et al., Journal of Experimental Medicine 169, 1721-1731, 1989). It is downregulated on mature granulocytes but retained on macrophages, monocytes and dendritic cells (Andrews et al., Blood 62, 24-132, 1983). Besides myelomonocytic cells, CD33 has also been found to be expressed on human mast cells and blood basophils (Valent et al., Blood 15; 73(7):1778-85, 1989,). Monoclonal antibodies directed against CD33 are used in diagnosis of leukemia as well as for therapeutic targeting and in vitro purging of bone marrow for autologous transplantation in acute myeloid leukemia (AML) (Duzkale et al., Biol Blood Marrow Transplant. 9(6):364-72, 2003). Initial efforts in therapeutic targeting focused on the development of immunotoxins using an anti-CD33 antibody conjugated to the toxin ricin. Since CD33 rapidly internalizes upon antibody binding (Audran et al., J Immunol Methods. 188(1): 147-54, 1995) the immunotoxin approach was obvious.

CD33 is a 67 KD transmembrane glycoprotein. The sialic acid-binding extracellular domain of CD33 is involved in cell-cell adhesion. The intracellular immunoreceptor tyrosine-based inhibitory motifs (ITIM) confer inhibitory signals to the cell, affecting proliferation and cell survival. The actual signalling pathways of CD33 are poorly understood but are assumed to involve the ITIM and ITIM-like motifs and the recruitment of tyrosine phosphatases (von Gunten et al., Ann. N.Y. Acad. Sci. 1143: 61-82, 2008). A murine CD33 orthologue has been defined but its functional comparability to human CD33 was questioned (Brinkman-Van der Linden et al., Mol Cell Biol., 23(12): 4199-206, 2003). The functional role of human CD33 on normal and malignant leukocytes remains unknown.

Several publications have described CD33 as a stable cell surface marker on primary AML and CML cells expressed by 70-100% of tested patients (Plesa et al., Cancer 112(3), 572-80, 2007, Hauswirt et al., Eur J Clin Invest. January 73-82, 2007, Scheinberg et al., Leukemia Vol. 3, 440-445, 1989). CD33 is expressed on malignant myeloid blast cells, which represent the majority of malignant cells in peripheral blood and bone marrow of leukemia patients, and on leukemic stem cells, a relatively small number of less differentiated cells in the bone marrow which are characterized by their capacity for self-renewal and the maintenance of the leukemic clonal hierarchy. Depletion of leukemic stem cells is regarded the key mechanism for sustained tumor free survival. The CD33 targeting immunotoxin Mylotarg®, a humanized IgG$_4$ antibody conjugated to the toxin chaliceamicin is used for the treatment of AML patients by delivering its toxic payload to CD33 positive AML cells (Amadori et al., Cancer Treat Rev. 34(1):49-60, 2008). Lintuzumab (SGN-33, HuM195), a "naked" CD33 specific humanized monoclonal antibody was evaluated in phase II clinical trials for the treatment of AML and MDS with initial clinical signs of efficacy from a phase I dose escalation study and tolerable adverse events being reported (Raza et al. Abstract #983, 14$^{th}$ EHA Congress, Jun. 4-7, 2009).

Targeting AML cell lines with CD33 specific HuM195 in vitro reduces TNF-α induced secretion of inflammatory cytokines like IL-8, MCP-1 and RANTES (Sutherland et al., Mabs 1:5, 481-490, 2009). The relevance of this effect for AML therapy is unknown but modulating the cytokine milieu of the tumor microenvironment may contribute to the therapeutic efficacy of the antibody. In addition, the antibody induces antibody-dependent cell-mediated cytotoxicity (ADCC) and antibody-dependent cell-mediated phagocytosis (ADCP) of AML cell lines in vitro (Sutherland et al., Mabs 1:5, 481-490, 2009). ADCC is considered to be a decisive mechanism for anti-tumor activity of antibodies in hematological malignancies. Data from clinical trials with the CD20-specific monoclonal antibody Rituximab have demonstrated the significance of effector cell mediated mechanisms for treatment of B-cell malignancies with respect to response to antibody treatment (Weng and Levy, J Clin Oncol. 21 (21): 3940-7, 2003).

In conclusion, it has been shown that CD33 antigen is expressed on normal cells of the myelomonocytic lineage and frequently expressed on tumor cells in myeloid leukemias. In a phase I trial with an antibody against CD33 (lintuzumab) first signs of efficacy were observed without severe adverse events. However, clinical development of lintuzumab was discontinued after results from a phase II trial in combination with chemotherapy did not yield the expected improvement in efficacy. Therefore, there is a clear need for the development of improved CD33-targeting treatment modalities.

In view of the prior art there is a need for providing a further improved therapy for myeloid cell malignancies and MDS, particularly for acute myeloid leukemia.

In particular there is a need for providing further improved antagonistic binding agents to CD33 for treating cancer, in particular AML.

SUMMARY OF THE INVENTION

The present invention provides novel CD33 binding agents binding to human CD33 and that are defined by
a) having a heavy chain variable region comprising CDR1, CDR2 and CDR3, and a light chain variable region comprising CDR4, CDR5 and CDR6, wherein CDR1 has an amino acid sequence selected from Seq ID No:29-42, CDR2 has an amino acid sequence selected from Seq ID No: 14-28, CDR3 has an amino acid sequence selected from Seq ID No:1-14, CDR4 has an amino acid sequence selected from Seq ID No:71-84, CDR5 has an amino acid sequence selected from Seq ID No:57-70, CDR6 has an amino acid sequence selected from Seq ID No:43-56, or
b) recognizing an epitope within the amino acid sequence FFHPIPYYDKNSPVHGYW (Seq ID No: 141) of human CD33.

The present invention further provides CD33 binding agents wherein the internalization kinetics of the CD33 binding agents are such that at least 30%, preferably 40%, of the initial amount of the antibody remain on the cell surface of HL60 cells at a time of 4 hours after incubation.

The present invention further provides CD33 binding agents, wherein the heavy chain variable region comprises an amino acid sequence selected from Seq ID No:85-98 and the light chain variable region comprises an amino acid sequence selected from Seq ID No:99-112.

The present invention further provides CD33 binding agents, wherein the heavy chain having an amino acid sequence selected from Seq ID No:113-126 and the light chain having an amino acid sequence selected from Seq ID No: 127-140.

The present invention further provides CD33 binding agents having mutations in the $F_c$ domain that increase ADCC.

Further preferred embodiments are outlined in the following specification and in the claims.

The CD33 binding agents according to the present invention have been found to have high affinity to human CD33 and further to have favourable internalization kinetics, which is characterized by a long presence of the CD33 binding agents when bound to CD33 on the surface of the target cells, which translates into favourable ADCC activity.

The inventors have also found that the CD33 binding agents according to the present invention bind to a different epitope of the extracellular domain of CD33 compared to Lintuzumab. Without wishing to be bound by any particular theory this is believed to be the reason for the different internalization kinetics of the CD33 binding agents according to the present invention and Lintuzumab.

DETAILED DESCRIPTION OF THE INVENTION

CD33 Binding Agents

Figure 1:
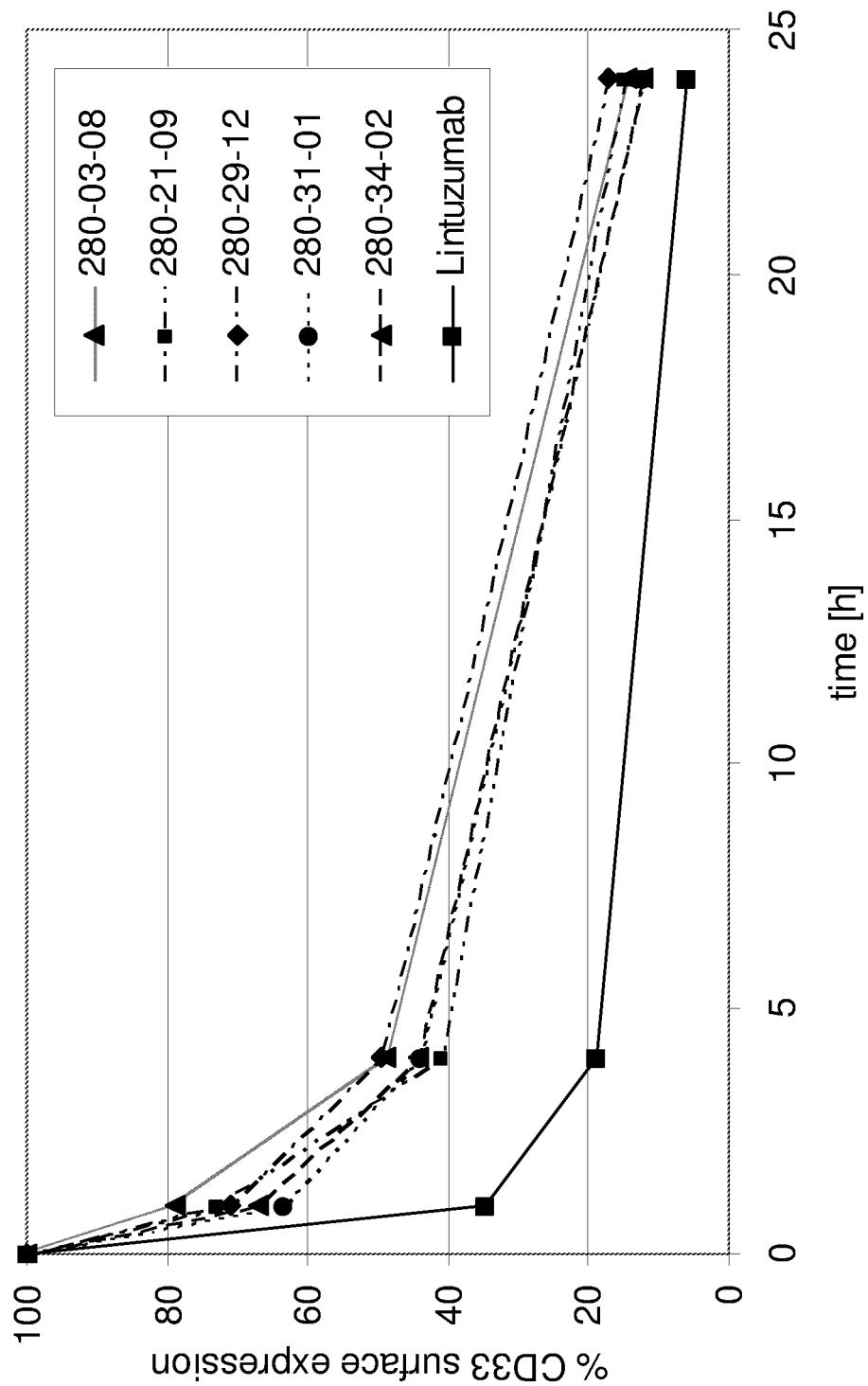
FIGS. 1-3 show the internalization of exemplary CD33 binding agents according to the invention in comparison to lintuzumab on HL60 cells.

The term "binding agent" as used herein means a protein or peptide that specifically binds to a target antigen. A binding agent can be, for example, an antibody, a derivative of such an antibody, or other agent that specifically binds to the target antigen. A binding agent can also be a protein comprising an Fv region or a portion thereof (e.g., a $V_H$ or $V_L$ or a CDR(s) of an antibody that specifically binds to the target antigen). In a preferred embodiment herein the binding agent is an antibody.

The term "CD33 binding agent" as used herein refers to a binding agent that specifically binds to CD33, typically a portion of the extracellular domain of human CD33.

The term "antibody" as used herein refers to (a) immunoglobulin polypeptides and immunologically active portions of immunoglobulin polypeptides (i.e., polypeptides of the immunoglobulin family, or fragments thereof, that contain an antigen binding site that immunospecifically binds to a specific target antigen), or (b) conservatively substituted derivatives of such immunoglobulin polypeptides or fragments that immunospecifically bind to the target antigen. Antibodies are generally described in, for example, Harlow and Lane, *Antibodies: A Laboratory Manual* (Cold Spring Harbor Laboratory Press, 1988). The term "antibody" refers to intact monoclonal antibodies, polyclonal antibodies, monospecific antibodies, multispecific antibodies (e.g., bispecific antibodies), and antibody fragments that exhibit the desired biological activity (e.g., antigen-binding). The antibody can be of any type or class (e.g., IgG, IgE, IgM, IgD, and IgA) or sub-class (e.g., IgG1, IgG2, IgG3, IgG4, IgA1 and IgA2), preferably of the IgG class, more preferably an IgG1.

An "intact" antibody is one which comprises an antigen-binding variable region as well as a light chain constant domain and heavy chain constant domains as appropriate for the antibody class. The constant domains may be native sequence constant domains (e.g., human native sequence constant domains) or amino acid sequence variants thereof.

An "antibody fragment" comprises a portion of an antibody, including the antigen-binding or variable region or a portion thereof. Examples of antibody fragments include Fab, Fab', F(ab')$_2$, and Fv fragments, $V_H$ and $V_L$ antigen binding fragments, diabodies, triabodies, tetrabodies, single-chain antibody, scFv, scFv-Fc, a SMIP, and multispecific antibodies formed from antibody fragment(s).

"Heavy chain variable region" or "$V_H$" means the part of the heavy chain comprising the CDR1, CDR2 and CDR3 and surrounding framework regions.

"Light chain variable region" or "$V_L$" means the part of the light chain comprising the CDR4, CDR5 and CDR6 and surrounding framework regions.

"CDR" means the hypervariable regions of the heavy and light chains, which determine the complementarity/binding specificity of an antibody or antibody fragment. The order of the CDRs in the present application is purely numerically.

"Epitope" herein means a part of an antigen, which is recognized by an antibody or antibody fragment. In particular this term refers to parts of CD33, which can be recognized by an antibody.

"mAbs" as used herein refers to monoclonal antibodies.

An antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC);

phagocytosis; down regulation of cell surface receptors (e.g., B cell receptor, BCR), etc.

"Single-chain Fv" or "scFv" antibody fragments comprise the $V_H$ and $V_L$ domains of an antibody, wherein these domains are present in a single polypeptide chain. The Fv polypeptide typically further comprises a polypeptide linker between the $V_H$ and $V_L$. domains which enables the scFv to form the desired structure for antigen-binding. For a review of scFv, see Plückthun in *The Pharmacology of Monoclonal Antibodies*, vol. 113, Rosenburg and Moore, eds., Springer-Verlag, New York, pp. 269-315 (1994).

A binding agent such as an antibody that is "directed to," "which binds" or that "specifically binds" an antigen of interest (i.e., a target antigen) is one capable of binding that antigen with sufficient affinity such that the binding agent is useful in targeting a cell expressing the antigen. Typically, the binding agent binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

An "antibody derivative" as used herein refers to an antibody, as defined above, that is modified by covalent attachment of a heterologous molecule such as, e.g., by attachment of a heterologous polypeptide, or by glycosylation, deglycosylation, acetylation or phosphorylation or other modification not normally associated with the antibody. In some embodiments, the heterologous molecule is not a therapeutic agent. In some embodiments, the heterologous molecule does not exhibit a cytostatic or cytotoxic effect by itself.

A further comprehensive reference for all terms and procedures used herein is Sambrook at al., *Molecular Cloning*, Cold Spring Harbor Laboratory Press; $3^{rd}$ edition (Jan. 15, 2001).

The CD33 binding agents specifically bind to a receptor, CD33, associated with a given target cell population. CD33 is a member of the sialoadhesion family that is expressed on cells of the hematopoietic lineage, including myeloid precursors, monocytes, macrophages, dendritic cells, and mast cells. CD33 is also expressed on tumor cells associated with myeloproliferative or mast cell proliferative diseases, including acute myeloid leukemia and myeloplastic syndromes, and on leukemic stem cells. Antibodies targeting CD33 and their uses have been generally described (see, e.g., Pierelli et al., 1993, *Br. J. Haematol.* 84:24-30; Matutes et al., 1985, *Hemaiol. Oncol.* 3: 179-186; Taussig et al., 2005, *Blood* 106:4086-4092; Florian et al., 2006, *Leuk. & Lymph.* 47:207-222).

In some embodiments, the CD33 binding agent is an antibody (e.g., a monoclonal antibody). Useful monoclonal antibodies can be homogeneous populations of antibodies to a CD33 (e.g., the extracellular domain of human CD33). A monoclonal antibody (mAb) can be prepared by using any technique known in the art. These include, but are not limited to the hybridoma technique originally described by Köhler and Milstein (1975, *Nature* 256:495-497), the human B cell hybridoma technique (Kozbor et al., 1983, *Immunology Today* 4:72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA and IgD and any subclass thereof. The hybridoma producing a monoclonal antibody may be cultivated in vitro or in vivo.

Useful monoclonal antibodies include, but are not limited to, human monoclonal antibodies, humanized monoclonal antibodies, chimeric monoclonal antibodies and functionally active antibody fragments of any of these.

Useful CD33 antibodies include antibodies that can achieve a therapeutic effect by various mechanisms known in the art, such as antibody-dependent cell-mediated cyotoxicity (ADCC), anti-dependent cell phagocytosis (ADCP) and/or complement dependent cytotoxicity (CDC). For example the antibody can mediate ADCC by interacting with immune effector cells such as NK cells, monocytes, and macrophages.

Recombinant antibodies, such as chimeric and humanized monoclonal antibodies, comprise both human and non-human portions, which can be made using standard recombinant DNA techniques. (See, e.g., Cabilly et al. U.S. Pat. No. 4,816,567; and Boss et al., U.S. Pat. No. 4,816,397; both of which are incorporated herein by reference in their entirety). "Humanized antibodies" are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0184187; European Patent Publication No. 0171496; European Patent Publication No. 0173494; International Publication No. WO 86/01533; U.S. Pat. No. 4,816,567; European Patent Publication No. 012023; Berter et al., 1988, Science 240: 1041-1043; Liu et al., 1987, Proc. Natl. Acad Set USA 84:3439-3443; Liu et al., 1987, J. Immunol. 139:3521-3526; Sun el al., 1987, Proc. Natl. Acad. Sci. USA 84:214-218; Nishimura et al., 1987, Cancer. Res. 47:999-1005; Wood et al. 1985, Nature 314:446-449; Shaw et al, 1988, J. Natl. Cancer Inst. 80: 1553-1559; Morrison, 1985, Science 229: 1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060: each of which is incorporated herein by reference in its entirety.

Human monoclonal antibodies may be made by any of numerous techniques known in the art (see, e.g., Teng el al., 1983, Proc. Natl. Acad. Sci. USA. 80:7308-7312; Kozbor et al, 1983, Immunology Today 4:72-79; Olsson at al., 1982, Meth. Enzymol. 92:3-16; and U.S. Pat. Nos. 5,939,598 and 5,770,429).

Fully human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a CD33 polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. Other human antibodies can be obtained commercially from, for example, Medarex (Princeton, N.J.), which are obtained by immunizing mice.

Fully human antibodies that recognize a selected epitope also can be generated using a technique referred to as "guided selection". In this approach a selected non-human monoclonal antibody, e.g., a mouse antibody, is used to guide the selection of a fully human antibody recognizing the same epitope. (See, e.g., Jespers el al, 1994, Biotechnology 12:899-903). Human antibodies also can be produced using various techniques known in the art, including phage display libraries (see, e.g., Hoogenboom and Winter, 1991, J. Mol. Biol 227:381; Marks et al, 1991, J Mol Biol 222:581; Quan and Carter, 2002, The rise of monoclonal antibodies as therapeutics, In Anti-IgE and Allergic Disease, Jardieu and Fick Jr., eds., Marcel Dekker, New York, N.Y., Chapter 20. pp. 427-469).

Useful antibody fragments include, but are not limited to, F(ab')$_2$ fragments, Fab' fragments, Fab fragments, Fvs, single chain antibodies (SCAs) (e.g., as described in U.S. Pat. No. 4,946,778: Bird, 1988, Science 242:423-42; Huston et al., 1988, Proc. Natl. Acad. Sci. USA 85:5879-5883; and Ward et al, 1989, Nature 334:544-54), scFv, scFv-Fc, FvdsFv, minibodies, diabodies, triabodies, tetrabodies, SMIPs (see, e.g., Published U.S. Patent Application No. 2005-0238646) and any other molecule comprising one or more CDRs and that has the same specificity as the antibody.

In other embodiments, the antibody is a fusion protein of an antibody, or a functionally active fragment thereof, joined to another protein. For example, an antibody or antibody fragment can be fused via a covalent bond (e.g., a peptide bond), at either the N-terminus or the C-terminus to an amino acid sequence of another protein (or portion thereof, typically at least a 10, 20 or 50 amino acid portion of the protein) that is not the antibody or an antibody fragment. In some embodiments, the antibody or fragment thereof can be covalently linked to the other protein at the C-terminus of the variable domain or a constant domain.

Antibodies can be modified, e.g., by the covalent attachment of any type of molecule as long as such covalent attachment permits the antibody to retain its antigen-binding immunospecificity. For example, a derivative of an antibody can be one that has been further modified, e.g., by glycosylation. de-glycosylation, acetylation, pegylation, phosphorylation, amidation. derealization by known protecting/blocking groups, proteolytic cleavage, linkage to another protein, etc. Any of numerous chemical modifications can be carried out by known techniques, including, but not limited to. specific chemical cleavage, acetylation, formylation, metabolic synthesis in the presence of tunicamycin, or the like. Additionally, the derivative can contain one or more unnatural amino acids.

In specific embodiments, it may be desirable to improve the binding affinity and/or other biological properties of the antibody. (See, e.g. U.S. Patent Publication Nos. 2006-0003412 and 2006-0008882). Amino acid sequence variants of the antibodies are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletions, insertions, and/or substitutions is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are favored locations for mutagenesis is called "alanine scanning mutagenesis" as described by Cunningham and Wells (1989, Science 244: 1081-1085). Here, a residue or group of target residues are identified (e.g., charged residues such as arg, asp, his. lys, and glu) and replaced by a neutral or negatively charged amino acid (typically alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions can include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide.

Another type of antibody is an amino acid substitution variant of an antibody. Such variants have at least one amino acid residue in the antibody molecule replaced by a different residue. The sites of greatest interest for substitutional mutagenesis include the hypervariable regions, but framework region alterations are also contemplated.

Substantial modifications in the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys. arg;
(5) residues that influence chain orientation: gly, pro; and
(6) aromatic: trp, tyr, phe.

Non-conservative substitutions will entail exchanging a member of one of these classes for another class.

It is desirable to modify the antibody with respect to effector function, e.g., so as to enhance antibody-dependent cell-mediated cyotoxicity (ADCC), anti-dependent cell phagocytosis (ADCP) and/or complement dependent cytotoxicity (CDC) of the antibody. In particular, the ADCC activity can be enhanced by introducing amino acid mutations in the constant region of the antibody (Lazar et al., PNAS 103, 11, 4005-4010, 2006). This may be achieved by introducing one or more amino acid substitutions in an Fc region of the antibody, see, e.g., Published U.S. Patent Application No. 2006-0160996. Alternatively or additionally, cysteine residue(s) may be introduced in the Fc region, thereby allowing interchain disulfide bond formation in this region. The homodimeric antibody thus generated may have improved internalization capability and/or increased CDC and ADCC. (See. e.g., Caron et al., 1992, J Exp. Med 176:1191-1195; and Shopes, 1992, J. Immunol. 148:2918-2922.) Homodimeric antibodies with enhanced anti-tumor activity may also be prepared using heterobifunctional cross-linkers as described in Wolff et al., 1993, Cancer Research 53:2560-2565. Alternatively, an antibody can be engineered which has dual Fc regions and may thereby have enhanced complement lysis and ADCC capabilities. (See. e.g., Stevenson et al. 1989, Anti-Cancer Drug Design 3:219-230.) A variety of modifications of the Fc region have been suggested in the art, both in the scientific literature and in patent documents, e.g. in EP 0307434, WO 9304173, WO 9734631, WO 9744362, WO 9805787, WO 9943713, WO 9951642, WO 9958572, WO 02060919, WO 03074679, WO 2004016750, WO 2004029207, WO 2004063351, WO 2004074455, WO 2004035752, WO 2004099249, WO 2005077981, WO 2005092925, WO 2006019447, WO 2006031994, WO 2006047350, WO 2006053301, WO 2006088494 and WO 2007041635.

In preferred embodiments, the antibodies of the invention are Fc variants with amino acid substitutions at positions 332 and/or 239 and/or 236. In preferred embodiments, the antibodies of the invention have mutations in the Fc domain selected from the group of
  i) a single substitution at position 332, preferably I332E;
  ii) a combination of substitutions at positions 239 and 332, preferably S239D/I332E;
  iii) a combination of substitutions at positions 236 and 332, preferably G236A/I332E;
  iv) a combination of substitutions at positions 236, 239 and, 332, preferably G236A/S239D/I332E.

In this context it is particularly preferred to introduce mutations in the $F_c$ domain at one or more positions selected from amino acids at positions 332 and/or 239 and/or 236 according to the Kabat EU numbering index. Particular preferred are substitutions at positions 239 and 332, especially S239D/I332E.

The Fc variants in the antibodies of the present invention are defined according to the amino acid modifications that compose them. Thus, for example, I332E is an Fc variant with the substitution I332E relative to the parent Fc polypeptide. Likewise, S239D/I332E defines an Fc variant with the substitutions S239D and I332E and S239D/I332E/G236A defines an Fc variant with the substitutions S239D, I332E, and G236A relative to the parent Fc polypeptide.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies may be glycosylated at conserved positions in their constant regions (see, e.g., Jefferis and Lund, 1997, Chem. Immunol. 65:11-128: Wright and Morrison, 1997, TibTECH 15:26-32). The oligosaccharide side chains of the immunoglobulins can affect the protein's function (see, e.g., Boyd et al., 1996, MoI. Immunol. 32: 1311-1318; Wittwe and Howard, 1990, Biochem. 29:4175-4180), and the intramolecular interaction between portions of the glycoprotein which can affect the conformation and presented three-dimensional surface of the glycoprotein (see, e.g., Jefferis and Lund, supra; Wyss and Wagner, 1996, Current Opin. Biotech. 7:409-416). Oligosaccharides may also serve to target a given glycoprotein to certain molecules based upon specific recognition structures. For example, it has been reported that in a galactosylated IgG, the oligosaccharide moiety 'flips' out of the inter-$C_H2$ space and terminal N-acetylglucosamine residues become available to bind mannose binding protein (see, e.g., Malhotra et al. 1995, Nature Med. 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL or CDC) (Boyd et al., 1996, MoI. Immunol. 32:131, 1-1318), while selective removal of sialic acid residues using neuraminidase resulted in no loss of CMCL. Glycosylation of antibodies has also been reported to affect ADCC. In particular, CHO cells with tetracycline-regulated expression of β(1.4)-N-acetylglucosaminyltransferase III (GnTIII), a glycosyltransferase catalyzing formation of bisecting GlcNAc, was reported to have improved ADCC activity (see, e.g., Umana et ai, 1999, Nature Biotech. 17: 176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalaciosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (i.e., glycosylation pattern), the extent of glycosylation, or the like.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence variants) or preparation by oligonucleotide-mediated (or site-directed) mutagenesis, PCR mutagenesis, or cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. (See, e.g., Hse el al., 1997, Biol. Chem. 272:9062-9070.) In addition to the choice of host cells, factors which affect glycosylation during recombinant production of antibodies include growth mode, media formulation, culture density, oxygenation, pH, purification schemes, and the like. Various methods have been proposed to alter the glycosylation pattern achieved in a particular host organism, including introducing or overexpressing certain enzymes involved in oligosaccharide production (see, e.g., U.S. Pat. Nos. 5,047,335; 5,510,261; and 5,278,299). Glycosylation, or certain types of glycosylation, can be enzymatically removed from the glycoprotein, for example using endoglycosidase H (Endo H). In addition, the recombinant host cell can be genetically engineered, e.g. made defective in processing certain types of polysaccharides. These and similar techniques are well known in the art.

The glycosylation structure of antibodies can be readily analyzed by conventional techniques of carbohydrate analysis, including lectin chromatography, NMR, mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation. en2ymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

The antibodies also can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631).

In its broadest aspect the present invention relates to CD33 binding agents binding to human CD33 and that are defined by
 a) having a heavy chain variable region comprising CDR1, CDR2 and CDR3, and a light chain variable region comprising CDR4, CDR5 and CDR6, wherein CDR1 has an amino acid sequence selected from Seq ID No:29-42, CDR2 has an amino acid sequence selected from Seq ID No: 15-28, CDR3 has an amino acid sequence selected from Seq ID No:1-14, CDR4 has an amino acid sequence selected from Seq ID No:71-84, CDR5 has an amino acid sequence selected from Seq ID No:57-70, CDR6 has an amino acid sequence selected from Seq ID No:43-56, or
 b) recognizing an epitope within the amino acid sequence FFHPIPYYDKNSPVHGYW (Seq ID No: 141) of human CD33.

The present invention further provides CD33 binding agents wherein the internalization kinetics of the CD33 binding agents are such that at least 30% of the initial amount of the antibody remain on the cell surface of HL60 cells at a time of 4 hours after incubation.

It has been found that the CD33 binding agents according to the present invention bind to a different epitope than lintuzumab, see example 4 herein. Both epitopes (Seq ID No: 141 and Seq ID No: 142) are non-overlapping. It is believed that the different epitopes on the extracellular domain of CD33, which are recognized by the CD33 binding agents according to the present invention and by lintuzumab, are the reason for the different internalization behaviour and ADCC performance of the CD33 binding agents according to the present invention and lintuzumab (cf. examples 2 and 3 herein).

In a preferred embodiment at least 40% of the initial amount of the CD33 binding agents remain on the cell surface at a time of 4 hours after incubation.

In a preferred embodiment the heavy chain variable region comprises an amino acid sequence selected from Seq ID No:85-98 and the light chain variable region comprises an amino acid sequence selected from Seq ID No:99-112.

In a preferred embodiment the CD33 binding agent has a heavy chain having an amino acid sequence selected from Seq ID No:113-126 and a light chain having an amino acid sequence selected from Seq ID No:127-140.

In a preferred embodiment the CD33 binding agent has an affinity to both human CD33 and cynomolgus CD33 with a $K_D$ of equal to or less than 10 nM.

In a preferred embodiment the CD33 binding agent is humanized.

In a preferred embodiment the CD33 binding agent is fully human.

In a preferred embodiment the CD33 binding agent further comprises an effector function.

In a preferred embodiment the effector function is mediated by an $F_c$ domain.

In a preferred embodiment the CD33 binding agent comprises one or more mutations in the $F_c$ domain that modulate the function of the $F_c$ domain.

In a preferred embodiment the modulation of the function of the $F_c$ domain is an increase of ADCC by at least 10%, preferably 50% or 100%.

Particularly preferred CD33 binding agents according to the present invention are listed in table 1:

TABLE 1

| Clone No | ID# | SeqID CDR1 | SeqID CDR2 | SeqID CDR3 | SeqID CDR4 | SeqID CDR5 | SeqID CDR6 | SeqID $V_H$ | SeqID $V_L$ | SeqID heavy chain | SeqID light chain |
|---|---|---|---|---|---|---|---|---|---|---|---|
| 1 | 280-03-08 | 29 | 15 | 1 | 71 | 57 | 43 | 85 | 99 | 113 | 127 |
| 2 | 280-21-09 | 30 | 16 | 2 | 72 | 58 | 44 | 86 | 100 | 114 | 128 |
| 3 | 280-29-12 | 31 | 17 | 3 | 73 | 59 | 45 | 87 | 101 | 115 | 129 |
| 4 | 280-31-01 | 32 | 18 | 4 | 74 | 60 | 46 | 88 | 102 | 116 | 130 |
| 5 | 280-31-01(mut) | 33 | 19 | 5 | 75 | 61 | 47 | 89 | 103 | 117 | 131 |
| 6 | 280-34-02 | 34 | 20 | 6 | 76 | 62 | 48 | 90 | 104 | 118 | 132 |

TABLE 1-continued

| Clone No | ID# | SeqID CDR1 | SeqID CDR2 | SeqID CDR3 | SeqID CDR4 | SeqID CDR5 | SeqID CDR6 | SeqID $V_H$ | SeqID $V_L$ | SeqID heavy chain | SeqID light chain |
|---|---|---|---|---|---|---|---|---|---|---|---|
| 7 | 280-50-01 | 35 | 21 | 7 | 77 | 63 | 49 | 91 | 105 | 119 | 133 |
| 8 | 280-50-01(mut) | 36 | 22 | 8 | 78 | 64 | 50 | 92 | 106 | 120 | 134 |
| 9 | 280-61-07 | 37 | 23 | 9 | 79 | 65 | 51 | 93 | 107 | 121 | 135 |
| 10 | 283-03-03 | 38 | 24 | 10 | 80 | 66 | 52 | 94 | 108 | 122 | 136 |
| 11 | 283-05-01 | 39 | 25 | 11 | 81 | 67 | 53 | 95 | 109 | 123 | 137 |
| 12 | 283-07-03 | 40 | 26 | 12 | 82 | 68 | 54 | 96 | 110 | 124 | 138 |
| 13 | 283-11-03 | 41 | 27 | 13 | 83 | 69 | 55 | 97 | 111 | 125 | 139 |
| 14 | 283-14-01 | 42 | 28 | 14 | 84 | 70 | 56 | 98 | 112 | 126 | 140 |

Treatment of Cancer

Several publications have described CD33 as a cell surface marker on primary AML and CML cells which is expressed on malignant cells of 70% to 100% of patients (Scheinberg et al 1989, Hauswirt et al 2007, Plesa et al 2007, Webber et al 2008). CD33 is expressed on malignant myeloid blast cells, which represent the majority of malignant cells in peripheral blood and bone marrow of leukemia patients, and on leukemic stem cells, a relatively small number of less differentiated cells in the bone marrow which are characterized by their capacity for self-renewal and the maintenance of the leukemic clonal hierarchy. The clinical feasibility of targeting CD33 using antibodies has been demonstrated by Mylotarg® (Gemtuzumab ozogamizin), an antibody-calicheamycin conjugate which was approved for the treatment of relapsed AML patients not eligible for other treatment options. An alternative approach directed towards CD33 is the development of lintuzumab (SGN-33, HuM195), a humanized IgG monoclonal antibody which has shown early signs of efficacy in clinical phase I trials (Raza et al., 2009). Taken together, there is a wealth of data, both preclinical and clinical, that underscore the relevance and feasibility of CD33 targeting for the treatment of AML and other CD33-positive malignancies.

Acute myeloid leukemia (AML) is a malignancy of the myeloid lineage of white blood cells. This hematological neoplasia is a blood and bone marrow disease that, if left untreated, is typically fatal within weeks to months. There is an estimated prevalence of 30000 cases of AML in the US and 47000 in the European Union (10 year prevalence data confirmed by Mattson-Jack, 2010). AML is the most prevalent form of adult acute leukemia (about 90%), comprising about 33% of new leukemia cases. The median age of patients diagnosed with AML is 67 years. AML accounts for about 1.2% of cancer deaths in the United States.

AML causes non-specific symptoms such as weight loss, fatigue, fever, and night sweats. AML is diagnosed by blood tests, bone marrow examination, and laboratory tests to determine the AML subtype and to determine treatment decisions.

Therapy for AML is highly depending on the age and performance status of the patient. Patients who can tolerate intensive induction (and subsequent consolidation and maintenance) chemotherapy will be treated intensely with a combination of cytotoxic drugs. These patients have a likelihood of achieving a complete response of approximately 75%. In this patient population the therapeutic goal is a cure. Still, relapse of AML occurs in about half of the patients within one year after achievement of a complete response. Long-term cure rates are in the 30% range. However, higher age at diagnosis or existence of co-morbidities does not allow administration of intensive induction therapy leading to a palliative treatment goal. Therefore, remission rates decline significantly in older patients with AML. The median survival of older patients with AML is less than 6 months.

In one aspect, the CD33 binding agents are useful for treating cancer, such as by delaying progression of a cancer and/or reducing cancer-associated cachexia, or preventing or delaying recurrence of a hematological malignancy (e.g., leukemia), in a mammal, preferably a human patient. The CD33 binding agent can be administered alone or co-administered with another therapeutic agent. In some embodiments, the CD33 binding agent is co-administered with a standard of care chemotherapeutic. The CD33 binding agent can be administered in an unconjugated form (i.e., not conjugated to a cytotoxin) or as a conjugate.

In this subsection, a "patient" is a human or other mammal who is undergoing treatment for, or has been diagnosed as having, cancer.

In some embodiments, the CD33 binding agents are useful for delaying progression of a cancer and/or reducing cancer-associated cachexia in a patient by administering to the patient in need thereof an effective dosage of the CD33 binding agent. Without being bound to a particular mechanism, the CD33 binding agent binds to effector or accessory cells of the myeloid or monocytic lineages (e.g., monocytes, macrophages, dendritic cells, and neutrophils), thereby inhibiting or reducing the production of various cytokines, chemokines and growth factors from the effector or accessory cells and/or the tumor cells. These cytokines, chemokines and growth factors, which can promote the growth and proliferation of tumor cells and/or contribute to cancer cachexia, include, but are not limited to, interleukin-1 (IL-1), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α). The CD33 binding agents also can reduce the migration of macrophages to the site of the tumor cells.

In some embodiments, administration of an effective dosage of a CD33 binding agent to a patient reduces the levels of at least one cytokine, chemokine or growth factor, which cytokine, chemokine or growth factor can promote the growth and proliferation of tumor cells, promote the migration of non-malignant effector cells, such as tumor associated macrophages (TAMS), to the vicinity of the tumor site and/or contribute to cancer cachexia. In specific embodiments, the cytokine, chemokine or growth factor is for example interleukin-1 (IL-1), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In another embodiment, a method is provided for delaying progression of a cancer by administering to a patient an effective regimen of a CD33 binding agent that can specifically bind to CD33. As a result of administration of the CD33 binding agent, the progression of the cancer is delayed, such as by reducing the growth or proliferation of the tumor cells, decreasing metastasis, reducing the level of at least one cytokine, chemokine or growth factor, reducing non-malignant effector cells in the vicinity of the tumor cells, or the like.

In another embodiment, a method is provided for reducing the tumor burden in a patient by administering to the patient an effective regimen of a CD33 binding agent that can specifically bind to CD33. As a result of administration of the CD33 binding agent, the tumor burden in the patient is arrested or reduced, such as by reducing the size or mass of the tumor, reducing the level of at least one cytokine, chemokine or growth factor, reducing non-malignant effector cells in the vicinity of the tumor cells, inhibiting the migration of macrophages in the vicinity of the tumor cells, reducing the number of non-malignant effector cells (e.g., TAMS or macrophages) in the tumor, or the like.

In another embodiment, a method is provided for reducing the tumor burden or delaying progression of a cancer in a patient by administering to the patient an effective regimen of a CD33 binding agent that can specifically bind to CD33. As a result of administration of the CD33 binding agent, the tumor burden in the patient is arrested or reduced, such as by recruiting immune effector cells like NK cells or macrophages or monocytes, which can destroy tumor cells by immune mediated mechanisms.

Antibody dependent cellular cytotoxicity (ADCC) is an immune effector cell mediated mechanism which may contribute to anti-tumor activity of monoclonal antibodies (Weiner G J. Monoclonal antibody mechanisms of action in cancer. Immunol Res. 2007; 39(1-3):271-8). The relevance of ADCC for anti-tumor efficacy has been demonstrated in preclinical models, e.g. in mouse tumor models (e.g. Clynes R A, Towers T L, Presta L G, Ravetch J V. Inhibitory Fc receptors modulate in vivo cytoxicity against tumor targets. Nat Med. 2000 April; 6(4):443-6).

Data from clinical trials support the relevance of ADCC for clinical efficacy of therapeutic antibodies (e.g. Weng W K, Levy R Two immunoglobulin G fragment C receptor polymorphisms independently predict response to rituximab in patients with follicular lymphoma. J Clin Oncol. 2003 Nov. 1; 21(21):3940-7. Epub 2003 Sep. 15). Interactions of monoclonal antibodies with Fc receptors on immune cells contribute to ADCC. The Fc of antibodies can be modified in order to display enhanced affinity to Fc receptors (e.g. Presta LG Engineering of therapeutic antibodies to minimize immunogenicity and optimize function. Adv Drug Deliv Rev. 2006 Aug. 7; 58(5-6):640-56. Epub 2006 May 23). Such enhanced affinity to Fc receptors results in increased ADCC activity which may lead to increased anti tumor efficacy in patients.

In the various embodiments described in this section, the CD33 binding agent can be used to treat a CD33 positive cancer (i.e., a cancer comprised of cancer cells that over express CD33 on their cell surface, or that express CD33 at levels considered acceptable for therapy with CD33 antibodies). The CD33 binding agent also can be used to treat a cancer that does not overexpress CD33 on the non-malignant effector cells relative to normal tissue of the same type. The cancer can be, for example, a non-hematological malignancy or a hematological malignancy. In specific examples, the hematological malignancy can be CD33-positive and can be, for example, acute lymphoid leukemia, acute myeloid leukemia, chronic myelomonocytic leukemia, an erythrocytic leukemia, acute megakaryoblastic leukemia, histiocytic lymphoma, a myeloid sarcoma, a mast cell proliferative disorder or myelodysplastic syndrome (MDS). In some embodiments, the hematological malignancy is a CD33-positive malignancy, such as acute myeloid leukemia or myelodysplastic syndrome (MDS).

In the various embodiments described in this section, the CD33 binding agent can be an unconjugated anti-CD33 antibody. For example, the antibody can be a fully human, humanized or chimeric antibody, such as a chimeric or humanized M 195 antibody. The antibody also can be another antibody, such as an antibody that competes with M 195 antibody for specific binding to CD33. The antibody also can bind to the same epitope as M 195 antibody or to a different epitope.

In other embodiments, the CD33 binding agent can be bound (i.e., conjugated) to a cytotoxin. The cytotoxin can be, for example, a peptide toxin, such as saporin, ricin, chlorotoxin, *pseudomonas* exotoxin, *pseudomonas* endotoxin or diphtheria toxin. The cytotoxin also can be a chemical (i.e., non-peptide-based) toxin, such as a calicheamicin, doxorubicin, a camptothecin, daunorubicin, or other DNA binding agents. The cytotoxin also can be an auristatin, a maytansinoid, a dolastatin, or other microtubule blocking agents.

A CD33 binding agent that is an anti-CD33 antibody can be administered to the patient intravenously or subcutaneously at a dose of 0.1 mg/kg or less to about 25 mg/kg, preferably 1.0 mg/kg to about 10 mg/kg. A CD33 binding agent that is an anti-CD33 antibody fragment or other CD33 binding protein can be administered in a dosage equivalent to a dose of 0.1 mg/kg to about 25 mg/kg. 1.0 mg/kg to about 10 mg/kg of intact antibody. The CD33 binding agent can be administered intravenously or subcutaneously to the patient on a schedule that is, for example, daily, weekly, biweekly, tri-weekly (i.e., every three weeks) or monthly, or a combination thereof, to the patient. The CD33 binding agent can be administered for a period of at least one month, at least two months, at least three months, at least four months, at least five month, at least six months, or more, as needed. In some embodiments, a treatment phase (supra) of the CD33 binding agent is followed by a maintenance phase, in which doses of the CD33 binding agent are administered less frequently than during the treatment phase. For example, maintenance doses can be administered weekly, biweekly, tri-weekly or monthly, for a period of 1-6 months. The dosages in the maintenance phase can be the same as the dosages in the treatment phase.

Treatment of a Hematological Malignancy in Remission

In another aspect, methods are provided of preventing or delaying recurrence of a hematological malignancy (e.g., leukemia) in a patient by administering to the patient in remission from the hematological malignancy an effective dosage of a CD33 binding agent, resulting in preventing or delaying recurrence of the underlying hematological malignancy. The CD33 binding agent specifically binds to CD33 on the surface of the hematological malignancy (i.e., leukemic cell) and/or to non-malignant effector cells.

In this disclosure, a "patient" is typically a human who is undergoing treatment for, or has been diagnosed as having, hematological malignancy. In some embodiments, the hematological malignancy is a CD33-positive hematological malignancy. Hematological malignancies include, but are not limited to, leukemias (e.g., acute lymphoblastic leukemia (ALL), acute myelogenous leukemia (AML), chronic myelogenous leukemia (CML), chronic myelomonocytic leukemia, hairy cell leukemia), Related blood disorders include, but are not limited to, myelodysplastic syndrome (MDS), myelofibrosis, myeloproliferative disease (e.g., polycythemia vera (PV. PCV or PRV), essential thrombocytosis (ET)), and amyloid due to light-chain disease.

The term "CD33-positive hematological malignancy" refers to a hematological malignancy characterized by the expression of CD33 on the surface of the malignant cells. CD33-positive hematological malignancies include, but are not limited to, acute myeloid leukemia (AML), chronic myeloid leukemia (CML), chronic myelomonocytic leukemia, thrombocyte leukemia, a myelodysplastic syndrome, a myeloproliferative disorder, refractory anemia, a preleukemia syndrome, a lymphoid leukemia, or an undifferentiated leukemia.

In some embodiments, the methods include administering to a patient in remission from a CD33 positive hematological malignancy an effective regimen of a CD33 binding agent, whereby the recurrence of the hematological malignancy is prevented or delayed. In some embodiments, the patient lacks detectable cells of the hematological malignancy. As used herein, a 'lack of detectable cells" is determined by standard diagnostic or prognostic methods. A patient in remission from AML typically exhibits resolution of abnormal clinical features, return to normal blood counts and normal hematopoiesis in the bone marrow with <5% blast cells, a neutrophil count of >1.000-1,500, a platelet count of >100,000, and disappearance of the leukemic clone. See, e.g., The Merck Manual, Sec. 11, Ch. 138 (17$^{th}$ ed. 1997): Estey, 2001, Cancer 92(5): 1059-1073.

The CD33 binding agent can be, for example, an antibody that specifically binds to CD33 and the hematological malignancy can be acute myeloid leukemia (AML), chronic myeloid leukemia (CML), chronic myelomonocytic leukemia, thymoid leukemia, a myelodysplastic syndrome, a myeloproliferative disorder, refractory anemia, a preleukemia syndrome, a lymphoid leukemia, or an undifferentiated leukemia.

In some embodiments, the patient in remission from the hematological malignancy has not undergone a bone marrow transplant. In other embodiments, the patient in remission from the hematological malignancy has undergone a bone marrow transplant. The bone marrow transplant can be either an autologous or an allogeneic bone marrow transplant.

The following cancer types are especially suitable to be treated by the antibodies according to the present invention:

Blood-borne cancers, including, but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblaslic leukemia, acute myelomonocytic leukemia, acule nonlymphocytic leukemia, acute undifferentiated leukemia, chronic myelocytic leukemia "CML", chronic lymphocytic leukemia "CLL", hairy cell leukemia, multiple myeloma.

Acute and chronic leukemias, which are suitable to be treated by CD33 binding agents include: lymphoblastic, myelogenous, lymphocytic, myelocytic leukemias and thrombocytic leukemia. Further myelodysplasia syndrome, myeloproliferative disorder, refractory anemia, preleukemia syndrome, lymphoid leukemia, or undifferentiated leukemia can be treated by CD33 binding agents.

Combinations with Other Active Substances

Depending on the disorder to be treated, the CD33 binding agents of the invention may be used on its own or in combination with one or more additional therapeutic agents, in particular selected from DNA damaging, DNA demethylating or tubulin binding agents or therapeutically active compounds that inhibit angiogenesis, signal transduction pathways or mitotic checkpoints in cancer cells or have immunomodulatory function (IMIDs).

The additional therapeutic agent may be administered simultaneously with, optionally as a component of the same pharmaceutical preparation, or before or after administration of the CD33 binding agent.

In certain embodiments, the additional therapeutic agent may be, without limitation, one or more inhibitors selected from the group of inhibitors of EGFR family, VEGFR family, VEGF, IGF-1R, Insulin receptors, AuroraA, AuroraB, PLK and PI3 kinase, FGFR, PDGFR, Raf, KSP or PDK1.

Further examples of additional therapeutic agents are inhibitors of CDKs, Akt, Src, Bcr-Abl, cKit, cMet/HGF, Her2, Her3, c-Myc, Flt3, HSP90, hedgehog antagonists, inhibitors of JAK/STAT, Mek, mTor, NFkappaB, the proteasome, Rho, an inhibitor of Wnt signaling or Notch signaling or an ubiquitination pathway inhibitor.

Further examples of additional therapeutic agents are inhibitors of DNA polymerase, topoisomerase II, multityrosine kinase inhibitors, CXCR4 antagonists, IL3RA inhibitors, RAR antagonists, KIR inhibitors, immunotherapeutic vaccines, TUB inhibitors, Hsp70 inducers, IAP family inhibitors, DNA methyltransferase inhibitors, TNF inhibitors, ErbB1 receptor tyrosine kinase inhibitors, multikinase inhibitors, JAK2 inhibitors, RR inhibitors, apoptosis inducers, HGPRTase inhibitors, histamine H2 receptor antagonists and CD25 receptor agnosists.

Examples for Aurora inhibitors are, without limitation, PHA-739358, AZD-1152, AT-9283, CYC-116, R-763, VX-667, MLN-8045, PF-3814735, SNS-314, VX-689, GSK-1070916, TTP-607, PHA-680626, MLN-8237, BI847325 and ENMD-2076.

Examples for PLK inhibitor are GSK-461364, BI2536 and BI6727.

Examples for raf inhibitors are BAY-73-4506 (also a VEGFR inhibitor), PLX-4032, RAF-265 (also a VEGFR inhibitor), sorafenib (also a VEGFR inhibitor), XL-281, Nevavar (also an inhibitor of the VEGFR) and PLX4032.

Examples for KSP inhibitors are ispinesib, ARRY-520, AZD-4877, CK-1122697, GSK-246053A, GSK-923295, MK-0731, SB-743921, LY-2523355, and EMD-534085.

Examples for a src and/or bcr-abl inhibitors are dasatinib, AZD-0530, bosutinib, XL-228 (also an IGF-1R inhibitor), nilotinib (also a PDGFR and cKit inhibitor), imatinib (also a cKit inhibitor), NS-187, KX2-391, AP-24534 (also an inhibitor of EGFR, FGFR, Tie2, Flt3), KM-80 and LS-104 (also an inhibitor of Flt3, Jak2).

An example for a PDK1 inhibitor is AR-12.

An example for a Rho inhibitor is BA-210.

Examples for PI3 kinase inhibitors are PX-866, PX-867, BEZ-235 (also an mTor inhibitor), XL-147, and XL-765 (also an mTor inhibitor), BGT-226, CDC-0941.

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, AV-299, ARQ-197, MetMAb, CGEN-241, BMS-777607, JNJ-38877605, PF-4217903, SGX-126, CEP-17940, AMG-458, INCB-028060, and E-7050.

An example for a c-Myc inhibitor is CX-3543.

Examples for Flt3 inhibitors are AC-220 (also an inhibitor of cKit and PDGFR), KW-2449, LS-104 (also an inhibitor of bcr-abl and Jak2), MC-2002, SB-1317, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are, tanespimycin, alvespimycin, IPI-504, STA-9090, MEDI-561, AUY-922, CNF-2024, and SNX-5422.

Examples for JAK/STAT inhibitors are CYT-997 (also interacting with tubulin), TG-101348 (also an inhibitor of Flt3), and XL-019.

Examples for Mek inhibitors are ARRY-142886, AS-703026, PD-325901, AZD-8330, ARRY-704, RDEA-119, and XL-518.

Examples for mTor inhibitors are temsirolimus, deforolimus (which also acts as a VEGF inhibitor), everolimus (a VEGF inhibitor in addition). XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are masitinib, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), sunitinib (also an inhibitor of Flt3, PDGFR, VEGFR), and XL-820 (also acts as a VEGFR- and PDGFR inhibitor), imatinib (also a bcr-abl inhibitor), nilotinib (also an inhibitor of bcr-abl and PDGFR).

Examples for hedgehog antagonists are IPI-609, CUR-61414, GDC-0449, IPI-926, and XL-139.

Examples for CDK inhibitors are seliciclib, AT-7519, P-276, ZK-CDK (also inhibiting VEGFR2 and PDGFR), PD-332991, R-547, SNS-032, PHA-690509, PHA-848125, and SCH-727965.

Examples for proteasome inhibitors are bortezomib, carfilzomib, and NPI-0052 (also an inhibitor of NFkappaB).

Examples for proteasome inhibitors/NFkappaB pathway inhibitors are bortezomib, carfilzomib, NPI-0052, CEP-18770, MLN-2238, PR-047, PR-957, AVE-8680, and SPC-839.

An example for an inhibitor of the ubiquitination pathway is HBX-41108.

Examples for demethylating agends are 5-azacitidine and decitabine.

Examples for anti-angiogenic agents are inhibitors of the FGFR, PDGFR and VEGF(R), and thalidomides, such agents being selected from, without limitation, bevacizumab, motesanib, CDP-791, SU-14813, telatinib, KRN-951, ZK-CDK (also an inhibitor of CDK), ABT-869, BMS-690514, RAF-265, IMC-KDR, IMC-18F1, IMiDs, thalidomide, CC-4047, lenalidomide, ENMD-0995, IMC-D1, Ki-23057, brivanib, cediranib, 1B3, CP-868596, IMC-3G3, R-1530 (also an inhibitor of Flt3), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, PF-337210, aflibercept, E-7080, CHIR-258, sorafenib tosylate (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL-880 (also an inhibitor of cMet), XL-647 (also an inhibitor of EGFR and EphB4), XL-820 (also an inhibitor of cKit), nilotinib (also an inhibitor of cKit and brc-abl), CYT-116, PTC-299, BMS-584622, CEP-11981, dovitinib, CY-2401401, ENMD-2976 and BIBF 120.

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, nimotuzumab, zalutumumab; examples for small molecule EGFR inhibitors are gefitinib, erlotinib, andetanib (also an inhibitor of the VEGFR) and afatinib (also an inhibitor of Her2). Another example for an EGFR modulator is the EGF fusion toxin.

Further EGFR and/or Her2 inhibitors useful for combination with an CD33 binding agent of the invention are lapatinib, trastuzumab, pertuzumab, XL-647, neratinib, BMS-599626 ARRY-334543, AV-412, mAB-806, BMS-690514, JNJ-26483327, AEE-788 (also an inhibitor of VEGFR), AZD-8931, ARRY-380 ARRY-333786, IMC-11F8, Zemab, TAK-285, AZD-4769, and afatinib (dual inhibitor of Her2 and EGFR).

DNA polymerase inhibitors useful in the combination with an CD33 binding agent of the invention are Ara-C/cytarabine, Clolar/clofarabine.

A DNA methyltransferase inhibitor useful in the combination with an CD33 binding agent of the invention is Vidaza/azacitidine.

An apoptosis inducer useful in the combination with an CD33 binding agent of the invention is Trisenox/arsenice trioxide.

Topoisomerase II inhibitors useful in the combination with an CD33 binding agent of the invention are idarubicin, daunorubicin and mitoxantrone.

A RAR antagonist useful in the combination with an CD33 binding agent of the invention is Vesanoid/tretinoin.

A HGPRTase inhibitor useful in the combination with an CD33 binding agent of the invention is Mercapto/mercaptopurine.

A histamine H2 receptor antagonist useful in the combination with an CD33 binding agent of the invention is Ceplene/histamine dihydrochloride.

A CD25 receptor agonist useful in the combination with an CD33 binding agent of the invention is IL-2.

The additional drug may also be selected from agents that target the IGF-1R and insulin receptor pathways. Such agents include antibodies that bind to IGF-1R (e.g. CP-751871, AMG-479, IMC-A12, MK-0646, AVE-1642, R-1507, BIIB-022, SCH-717454, rhu Mab IGFR and novel chemical entities that target the kinase domain of the IGF1-R (e.g. OSI-906 or BMS-554417, XL-228, BMS-754807).

Other agents that may be advantageously combined in a therapy with the CD33 binding agent of the invention are molecules targeting CD20, including CD20 specific antibodies like rituximab, LY-2469298, ocrelizumab, MEDI-552, IMMU-106, GA-101 (=R7159), XmAb-0367, ofatumumab, radiolabbeled CD20 antibodies, like tositumumab and ibritumomab tiuxetan or other CD20 directed proteins, like the SMIP Tru015, PRO-131921, FBT-A05, veltuzumab, R-7159.

CD33 binding agents may be combined with inhibitors of other surface antigens expressed on leukocytes, in particular antibodies or antibody-like molecules, e.g. anti-CD2 (siplizumab), anti-CD4 (zanolimumab), anti-CD19 (MT-103, MDX-1342, SAR-3419, XmAb-5574), anti-CD22 (epratuzumab), anti-CD23 (lumiliximab), anti-CD30 (iratumumab), anti-CD32B (MGA-321), anti-CD38 (HuMax-CD38), anti-CD40 (SGN40), anti-CD52 (alemtuzumab), anti-CD80 (galiximab).

Other agents to be combined with CD33 binding agents are immunotoxins like BL-22 (an anti-CD22 immunotoxin), inotuzumab ozogamicin (an anti-CD23 antibody-calicheamicin conjugate), RFT5.dgA (anti-CD25 Ricin toxin A-chain), SGN-35 (an anti-CD30-auristatin E conjugate), and gemtuzumab ozogamicin (an anti-CD33 calicheamicin conjugate), MDX-1411 (anti-CD70 conjugate). or radiolabelled antibodies like $^{90}$Y-epratuzumab (anti-CD22 radioimmunoconjugate).

In addition, CD33 binding agents may be combined with immunomodulators, agents, e.g. antibodies, that induce apoptosis or modify signal transduction pathways like the TRAIL receptor modulators mapatumumab (a TRAIL-1 receptor agonist), lexatumumab (a TRAIL-2 receptor agonist), tigatuzumab, Apomab, AMG-951 and AMG-655; an anti-HLA-DR antibody (like 1D09C3), an anti-CD74, an osteoclast differentiation factor ligand inhibitor (like denosumab), a BAFF antagonist (like AMG-623a) or an agonist of a Toll-like receptor (e.g. TLR-4 or TLR-9).

Other drugs that may be used in combination with the CD33 binding agents of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortinsone, fluoxymesterone, medroxyprogesterone, hydroxyprogesterone caproate, diethylstilbestrol, testosterone propionate, fluoxymesterone/equivalents, octreotide, arzoxifene, pasireotide, vapreotide, adrenocorticosteroids/antagonists, prednisone, dexamethasone, ainoglutethimide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, trimetrexate, pemetrexed, pyrimidine analogues like 5-fluorouracil, fluorodeoxyuridine, capecitabine, decitabine, nelarabine, 5-azacytidine, and gemcitabine, purine and adenosine analogues such as mercaptopurine, thioguanine, azathioprine, cladribine and pentostatin, cytarabine, fludarabine, clofarabine); antitumor antibiotics (e.g. anthracyclines like doxorubicin, daunorubicin, epirubicin and idarubicin, mitomycin-C, bleomycin dactinomycin, plicamycin, splicamycin, actimomycin D, mitoxantrone, mitoxantroneidarubicin, pixantrone, streptozocin, aphidicolin); platinum derivatives (e.g. cisplatin, oxaliplatin, carboplatin, lobaplatin, satraplatin); alkylating agents (e.g. estramustine, semustine, mechlorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan, banoxantrone, camptothecin) and miscellaneous chemotherapeutics such as retinoic acid derivatives, amifostine, anagrelide, interferon alpha, interferon beta, interferon gamma, interleukin-2, procarbazine, N-methylhydrazine, mitotane, and porfimer, bexarotene, celecoxib, ethylenemine/methyl-melamine, thriethyienemelamine, triethylene thiophosphoramide, hexamethylmelamine, and enzymes L-asparaginase, L-arginase and metronidazole, misonidazole, desmethylmisonidazole, pimonidazole, etanidazole, nimorazole, RSU 1069, E09, RB 6145, SR4233, nicotinamide, 5-bromodeozyuridine, 5-iododeoxyuridine, bromodeoxycytidine, erythrohydroxynonyl-adenine, anthracenedione, GRN-163L (a competitive telomerase template antagonist), SDX-101 (a PPAR agonist), talabostat (a DPP inhibitor), forodesine (a PNP inhibitor), atacicept (a soluble receptor targeting TNF family members BLyS and APRIL), TNF-alpha neutralizing agents (Enbrel, Humira, Remicade), XL-844 (a CHK1/2 inhibitor), VNP-40101M (a DNA alkylating agent), SPC-2996 (an antisense bcl2 inhibitor), obatoclax (a bcl2 inhibitor), enzastaurin (a PKC beta modulator), vorinistat (an HDAC inhibitor), romidepsin (an HDAC inhibitor), AT-101 (a Bcl-2/Bcl-xL inhibitor), plitidepsin (a multi-actioned depsipeptide), SL-11047 (a polyamine metabolism modulators).

The CD33 binding agents of the invention may also be used in combination with other therapies including surgery, stem cell transplantation, radiotherapy, endocrine therapy, biologic response modifiers, hyperthermia and cryotherapy and agents to attenuate any adverse effect (e.g. antiemetics), G-CSF, GM-CSF, photosensitizers such as hematoporphyrin derivatives, Photofrin, benzoporphyrin derivatives, Npe6, tin etioporphyrin, pheoboride-a bacteriochlorophyll-a, naphthalocyanines, phthalocyanines, zinc phthalocyanines.

Pharmaceutical Compositions and Methods of Administration

The CD33 binding agents can be in any form that allows for the composition to be administered to a patient. For example, the composition can be in the form of a solid or liquid. The preferred mode of application is parenteral, by infusion or injection (intraveneous, intramuscular, subcutaneous, intraperitoneal, intradermal), but other modes of application such as by inhalation, transdermal, intranasal, buccal, oral and intra-tumor may also be applicable. Parenteral administration includes subcutaneous injections, intravenous, intramuscular, intrastemal injection or infusion techniques. In one aspect, the compositions are administered parenterally. In yet another aspect, the compounds are administered intravenously.

Pharmaceutical compositions can be formulated so as to allow a compound to be bioavailable upon administration of the composition to a patient. Compositions can take the form of one or more dosage units, where, for example, a container of a compound in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of patient (e.g., human), the particular form of the compound, the manner of administration, and the composition employed.

The pharmaceutically acceptable carrier or vehicle can be particulate, so that the compositions are, for example, in powder form. The carrier(s) can be liquid, with the compositions being, for example, an injectable liquid. The composition can be in the form of a liquid, e.g., for parenteral injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono- or digylcerides which can serve as the solvent or suspending medium, polyethylene glycols, glycerin, cyclodextrin, propylene glycol or other solvents; stabilizers such as amino acids; surfactants such as polysorbates; antibacterial agents such as benzyl alcohol or methyl paraben; antioxidants such as ascorbic acid or sodium bisulfite; chelating agents such as ethylenediaminetetraacelic acid; buffers such as acetates, citrates or phosphates; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The CD33 binding agents may also be dried (freeze-dried, spray-dried, spray-freeze dried, dried by near or supercritical gases, vacuum dried, air-dried), precipitated or crystallized or entrapped in microcapsules that are prepared, for example, by coacervation techniques or by interfacial polymerization using, for example, hydroxymethylcellulose or gelatin and poly-(methylmethacylate), respectively, in colloidal drug delivery systems (for example, liposomes, albumin microspheres, microemulsions, nano-particles and nanocapsules), in macroemulsions or precipitated or immobilized onto carriers or surfaces, for example by pcmc technology (protein coated microcrystals). Such techniques are disclosed in Remington: The Science and Practice of Pharmacy, 21$^{st}$ edition, Hendrickson R. Ed.

The amount of the composition that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a drug(s) or agent(s) such that a suitable dosage will be obtained. Typically, this amount is at least about 0.01% of a drug or agent by weight of the composition. When intended for oral administration, this amount can be varied to range from about 0.1% to about 80% by weight of the composition. In one aspect, oral compositions can comprise from about 4% to about 50% of the compound by weight of the composition. In yet another aspect, present compositions are prepared so that a parenteral dosage unit contains from about 0.01% to about 2% by weight of the compound.

For intravenous administration, the composition can comprise from about 1 to about 50 mg of a drug or agent per kg of the patient's body weight. In one aspect, the composition can include from about 1, 1.5 or 2.5 to about 50 mg of a drug or agent per kg of the patient's body weight. In another aspect, the amount administered will be in the range from about 1, 1.5 or 2.5 to about 25 mg/kg of body weight of a drug or agent.

In some embodiments, the dosage administered to a patient is less than 0.1 mg/kg to about 50 mg/kg of the patient's body weight. (For conversion to mg/mm$^2$, a BSA of 1.8 m$^2$ and a body weight of 80 kg can be used.) As discussed herein, a CD33 binding agent can be administered intravenously or subcutaneously to the patient on a schedule that is, for example, daily, weekly, biweekly, tri-weekly or monthly to the patient. For example, a CD33 binding agent can be administered weekly, for a period of 2 to 10 weeks, typically 3-6 weeks. In some embodiments, the dosage regimen of the CD33 binding agent maintains a blood serum concentration of antibody at least 5 µg/ml or at least 10 µg/ml during the dosage cycle. The CD33 binding agent can be administered, for example, from 1-8, or more cycles. In some embodiments, a CD33 binding agent is administered chronically to a subject.

By way of example, the invention includes a method of treating a cancer, such as myeloid leukemia, by administering 0.1 mg/kg to 50 mg/kg, for instance about 1.5-8 or 2.5-8 mg/kg, of an anti-CD33 antibody according to the invention weekly.

This treatment can be usually be continued for about 1-3 months, typically about two months. In an embodiment, the dosing schedule is maintained until a reduction in blasts is noted. For example, dosing can be continued up to about 6 months. This treatment can be followed by a less frequent dosing schedule, involving for instance biweekly doses (or twice per month). This dosing schedule can be maintained 1, 2, 3, 4, 5, 6 months or more to maintain a reduction in blasts and/or a remission.

In some embodiments, a prophylactic agent can be administered with a CD33 binding agent to minimize infusion reactions. Suitable prophylactic agents include, for example, methyl prednisolone, diphenyldramine, acetaminophen or other suitable agent. The prophylactic agent can be administered prior to or at about the same time as the CD33 binding agent.

The drug(s) or agent(s) or compositions can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a compound. In certain embodiments, more than one drug or agent or composition is administered to a patient.

It can be desirable to administer one or more drugs or agents or compositions locally to the area in need of treatment, as appropriate for the drug or agent. This can be achieved, for example, and not by way of limitation, by local infusion during surgery; topical application, e.g., in conjunction with a wound dressing after surgery; by injection: by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue.

The drug(s) or agent(s) or compositions can be delivered in a controlled release system, such as a pump or various polymeric materials. In yet another embodiment, a controlled-release system can be placed in proximity of the target of the drug(s) or agent(s) or compositions, thus requiring only a fraction of the systemic dose (see, e.g., Goodson, in Medical Applications of Controlled Release, vol. 2, pp. 115-138 (1984)). Other controlled-release systems discussed in the review by Langer (1990, Science 249: 1527-1533) can be used.

The drugs or agents are formulated in accordance with routine procedures as a pharmaceutical composition adapted for intravenous administration to animals, particularly human beings, as appropriate for the drug or agent. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where drug or agent is to be administered by infusion, it can be dispensed, for example, with an infusion bottle containing sterile pharmaceutical grade water or saline. Where the drug or agent is administered by injection, an ampoule of sterile water for injection or saline can be provided so that the ingredients can be mixed prior to administration.

Compositions of therapeutic agents also can be administered according to accepted dosage forms in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered drugs or agents. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can be administered to a patient in need thereof at a frequency, or over a period of time, that is determined by the attending physician. The compositions can be administered over a period of 1 day, 2 days, 3 days, 5 days, 7 days, 10 days, 14 days, 21 days, 28 days, one month, two months, or longer periods of time. It is understood that the compositions can be administered for any period of time between 1 day and two months or longer.

Production of Antibodies

Antibodies can be produced using any method useful for the synthesis of antibodies, in particular, such as by recombinant expression or chemical synthesis.

Recombinant expression of antibodies, or fragments or derivatives thereof, typically involves construction of a nucleic acid that encodes the antibody. If the nucleotide sequence of the antibody is known, a nucleic acid encoding the antibody or a polypeptide thereof maybe assembled from chemically synthesized oligonucleotides (e.g., as described in Kutmeier at al., 1994, BioTechniques 17:242), which involves the synthesis of overlapping oligonucleotides containing portions of the sequence encoding the antibody, annealing and ligation of those oligonucleotides, and then amplification of the ligated oligonucleotides, e.g., by PCR.

Alternatively, a nucleic acid molecule encoding an antibody or a polypeptide thereof can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by, e.g., PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin is not available), antibodies specific for a particular antigen can be generated by any method known in the art, for example, by immunizing a patient, or suitable animal model such as a rabbit or mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985, in Monoclonal Antibodies and Cancer Therapy, Alan R. Liss, Inc., pp. 77-96). Alternatively, a clone encoding at least the Fab portion of the antibody can be obtained by screening Fab expression libraries (e.g., as described in Huse et al., 1989, Science 246, 1275-1281) for clones of Fab fragments that bind the specific antigen or by screening antibody libraries (see, e.g., Clackson et al, 1991, Nature 352:624; Hane et al, 1997, Proc. Natl. Acad. Sci. USA 94:4937).

Once a nucleic acid sequence encoding at least the variable domain of the antibody is obtained, it can be introduced into a vector containing the nucleotide sequence encoding the constant regions of the antibody (see, e.g., International Publication No. WO 86/05807; WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis and in vitro site directed mutagenesis (see, e.g., Hutchinson et al, 1978, J. Biol. Chem. 253:6551).

In addition, techniques have been developed for the production of "chimeric antibodies" (see, e.g., Morrison et al., 1984, Proc. Natl. Acad. Sci. USA 81: 851-855; Neuberger et al., 1984, Nature 312:604-608; Takeda et al., 1985, Nature 314:452-454). A chimeric antibody is a molecule in which different portions are derived from different animal species, such as those having a variable region derived from a murine monoclonal antibody and a human immunoglobulin constant region, e.g., humanized antibodies.

Once a nucleic acid sequence encoding an antibody has been obtained, the vector for the production of the antibody can be produced by recombinant DNA technology using techniques known in the art. Methods that are known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al (1990, Molecular Cloning, A Laboratory Manual. $2^{nd}$ Ed., Cold Spring Harbor Laboratory, Cold Spring Harbor, N.Y.; and Sambrook et al., 2001; Molecular Cloning, A Laboratory Manual, $3^{rd}$ Ed., Cold Spring Harbor Publish., Cold Spring Harbor, N.Y.) and Ausubel et al. (eds., 1993-2006, Current Protocols in Molecular Biology, John Wiley & Sons, NY).

An expression vector comprising the nucleotide sequence of an antibody or the nucleotide sequence of an antibody can be transferred to a host cell by conventional techniques (e.g., electroporation, liposomal transaction, calcium phosphate precipitation or transduction), and the resulting cells are then cultured by conventional techniques to produce the antibody. In specific embodiments, the expression of the antibody is regulated by a constitutive, an inducible or a tissue-specific promoter.

The host cells used to express the recombinant antibody can be either bacterial cells such as *Escherichia coli*, or, preferably, eukaryotic cells, especially for the expression of recombinant immunoglobulin molecules. In particular, mammalian cells such as Chinese hamster ovary cells (CHO), in conjunction with a vector containing the major intermediate early gene promoter element from human cytomegalovirus is an effective expression system for immunoglobulins (see, e.g., Foecking et al., 1986, Gene 45:101; Cockett el al., 1990, BioTechnology 8:2). The CHO cell line can be, for example, DG44 or CHO-S. In another example, an antibody can be expressed using the CHEF system. (See, e.g., U.S. Pat. No. 5,888,809.)

A variety of other host-expression vector systems can be utilized to express antibodies. Such host-expression systems represent vehicles by which the coding sequences of the antibody can be produced and subsequently purified, but also represent cells that can, when transformed or transfected with the appropriate nucleotide coding sequences, express an antibody immunoglobulin molecule in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing antibody coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing antibody coding sequences; or mammalian cell systems (e.g., COS, CHO, CHO-S, BH, 293, 293T or 3T3 cells) harboring recombinant expression constructs containing promoters derived from the genome of mammalian cells (e.g., metallothionein promoter) or from mammalian viruses (e.g., the adenovirus late promoter, the vaccinia virus 7.5K promoter).

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited to, the *E. coli* expression vector pUR278 (Ruther et al, 1983, EMBOJ. 2:1791-94), in which the antibody coding sequence may be ligated individually into the vector in frame with the lac Z coding region so that a fusion protein is produced; pIN vectors (Inouye and Inouye, 1985, Nucleic Acids Res. 13:3101-3109; Van Heeke and Schuster, 1989, J. Biol. Chem. 24:5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) or the analogous virus from *Drosophila melanogaster* can be used as a vector to express foreign genes. The virus grows in Spodopiera frugipenta cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (See, e.g., Logan and Shenk, 1984, Proc. Natl. Acad. Sci. USA 81:355-359). Specific initiation signals can also be required for efficient translation of inserted antibody coding sequences. These signals include the ATG initiation codon and adjacent sequences. Furthermore, the initiation codon is operably related to the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen to modulate the expression of the inserted sequences, or modify and process the gene product in the specific fashion desired.

Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO (e.g., DG44 or CHO-S), VERY, BH, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody. Such engineered cell lines can be particularly useful in screening and evaluation of tumor antigens that interact directly or indirectly with the antibody.

A number of selection systems can be used. For example, the herpes simplex virus thymidine kinase (see, e.g., Wigler el al., 1977, Cell 11:223), hypoxanthine-guanine phosphoribosyltransferase (see, e.g., Szybalska and Szybalski, 1992, Proc. Natl Acad. Sci. USA 48:202), and adenine phosphoribosyltransferase (see, e.g., Lowy et al., 1980, Cell 22:817) genes can be employed in tk-, hgprt- or aprt-cells, respectively. Also, antimetabolite resistance can be used as the basis of selection for the following genes: DHFR, which confers resistance to methotrexate (see e.g., Wigler el al., 1980, Proc. Natl. Acad Sci. USA 77:3567-70; O'Hare et al., 1981, Proc. Natl. Acad. Sci. USA 78: 1527-31); gpt, which confers resistance to mycophenolic acid (see, e.g., Mulligan and Berg, 1981, Proc. Natl. Acad. Sci. USA 78:2072-76); neo, which confers resistance to the aminoglycoside G-418 (see, e.g. Clinical Pharmacy 12:488-505; Wu and Wu, 1991, Biotherapy 3:87-95; Tolstoshev, 1993, Arm. Rev. Pharmacol. Toxicol. 32:573-596; Mulligan, 1993, Science 260:926-932; Morgan and Anderson, 1993, Ann. Rev. Biochem. 62:191-217; and May, 1993, TIB TECH 11(5): 155-215) and hygro, which confers resistance to hygromycin (see, e.g., Santerre et al., 1984, Gene 30:147-50). Methods commonly known in the art of recombinant DNA technology which can be used are described in Ausubel et al. (eds., 1993-2006, Current Protocols in Molecular Biology. John Wiley & Sons, NY; Kriegler, 1990, Gene Transfer and Expression. A laboratory Manual, Stockton Press, NY; and in Chapters 12 and 13, Dracopoli et al. (eds., 1994, Current Protocols in Human Genetics, John Wiley & Sons, NY; and Colberre-Garapin et al, 1981, 7. MoI. Biol. 150:1-14).

The expression levels of an antibody can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (see, e.g., Crouse et al., 1983, Mol. Cell. Biol. 3:257-66).

The host cell can be co-transfected with two expression vectors, the first vector encoding a heavy chain derived polypeptide and the second vector encoding a light chain derived polypeptide. The two vectors can contain the same or different selectable markers that enable equal expression of heavy and light chain polypeptides. Alternatively, a single vector can be used to encode both heavy and light chain polypeptides. In such situations, the light chain is typically placed before the heavy chain to avoid an excess of toxic free heavy chain (see, e.g., Proudfoot, 1986, Nature 322: 562-65; Kohler, 1980, Proc. Natl. Acad. Sci. USA 77:2197-9). The coding sequences for the heavy and light chains can comprise cDNA or genomic DNA.

Once the antibody has been recombinantly expressed, it can be purified using any suitable method for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

A comprehensive reference for all steps used for making the monoclonal antibodies according to the present invention is Yokoyama et al., "Production of Monoclonal Antibodies", Current Protocols in Immunology, Unit 2.5, 2006.

EXAMPLES

Example 1. Affinitity to CD33

The CD33 binding agents have a $K_D$ to both human and cynomolgus CD33 of Affinities of 10 nM or less on the cell line HL60 and HEK293-cynomolgus CD33, respectively.

Fourteen CD33 binding agents (fully human monoclonal antibodies as listed in table 1 as No. 1-14, respectively) to human and cynomolgus CD33 were determined by FACS Scatchard analysis as described in Brockhoff et al., (Cytometry. 1994 Sep. 1; 17(1):75-83) on CD33 expressing cells (AML-derived HL60 cell line, recombinant HEK293-cynomolgusCD33 cell line). Briefly, dilutions of a CD33 binding agent were prepared in a 96 well plate starting with 100-400 nM in the first well (80 pil), followed by 11 dilution steps (1:2, 40+40 µl). 50 µl of CD33 binding agent dilutions are added to FACS tubes, 150 µl cells ($0.8 \times 10^6$/ml=$1.2 \times 10^5$ cells/tube) are added to each FACS tube. Cells were gently mixed and incubated for 1 h on ice. Thereafter 50 µl FITC conjugated secondary antibody (concentration 15 µg/ml; mouse mAb anti-human IgG) was added, mixed, and incubated for 30 min. on ice. 4 ml PBS ph7.2 containing 0.02% acid were added thereafter, cells were pelleted and resuspended in 300 µl PBS pH 7.2 and subjected to FACS analysis using a BD FACS Canto. All experimental steps were performed on wet ice, all CD33 binding agent dilutions were made in PBS/0.5% BSA+0.02% acid. FACS calibration was performed using Quantum FITC MESF (Premix) Beads (Bangs Laboratories). All samples were measured using the same FACS parameters. The ratio of bound IgG versus free IgG was calculated from MFI values at different CD33 binding agent concentrations and displayed as Scatchard blot. A regression line was drawn through the resulting data points, the slope of this line corresponds to the negative value of the association constant. The results are listed in table 2.

TABLE 2

| No | Clone ID # | Human CD33 $K_D$ (nM) | Cynomolgus CD33 $K_D$ (nM) |
|---|---|---|---|
| 1 | 280-03-08 | 0.3 | 0.03 |
| 2 | 280-21-09 | 0.4 | 0.3 |
| 3 | 280-29-12 | 0.5 | 0.6 |
| 4 | 280-31-01 | 0.4 | 0.3 |
| 5 | 280-31-01 (mut) | 1 | 0.5 |
| 6 | 280-34-02 | 0.3 | 0.5 |
| 7 | 280-50-01 | 0.3 | 0.5 |
| 8 | 280-50-01 (mut) | 0.4 | 1.7 |
| 9 | 280-61-07 | 0.3 | 0.4 |
| 10 | 283-03-03 | 0.3 | 1.9 |
| 11 | 283-05-01 | 0.2 | 1.1 |
| 12 | 283-07-03 | 0.3 | 2.1 |
| 13 | 283-11-03 | 0.3 | 0.6 |
| 14 | 283-14-01 | 3.2 | 2.3 |

Example 2: Internalization Kinetics

Figure 2:
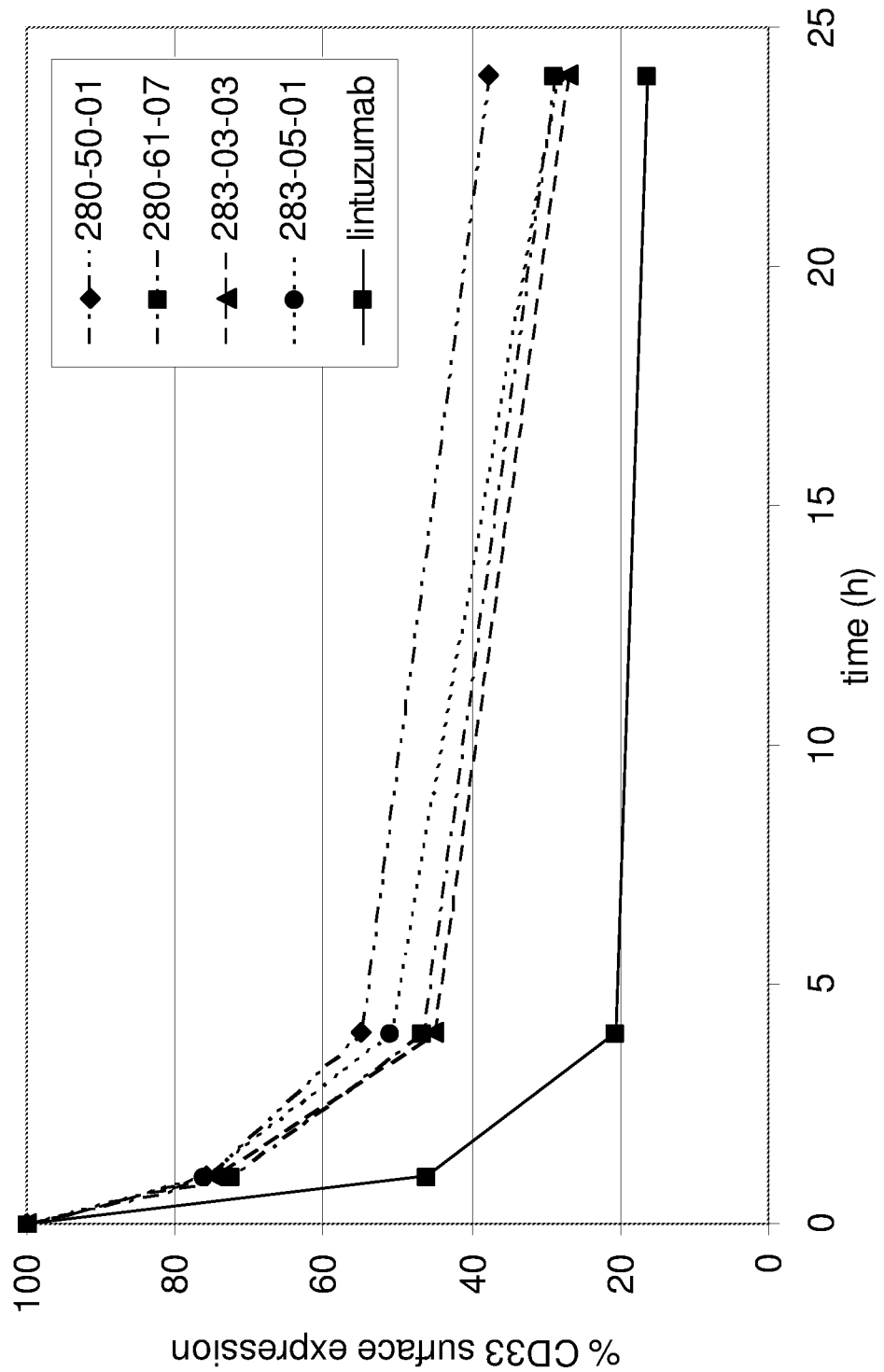
Figure 3:
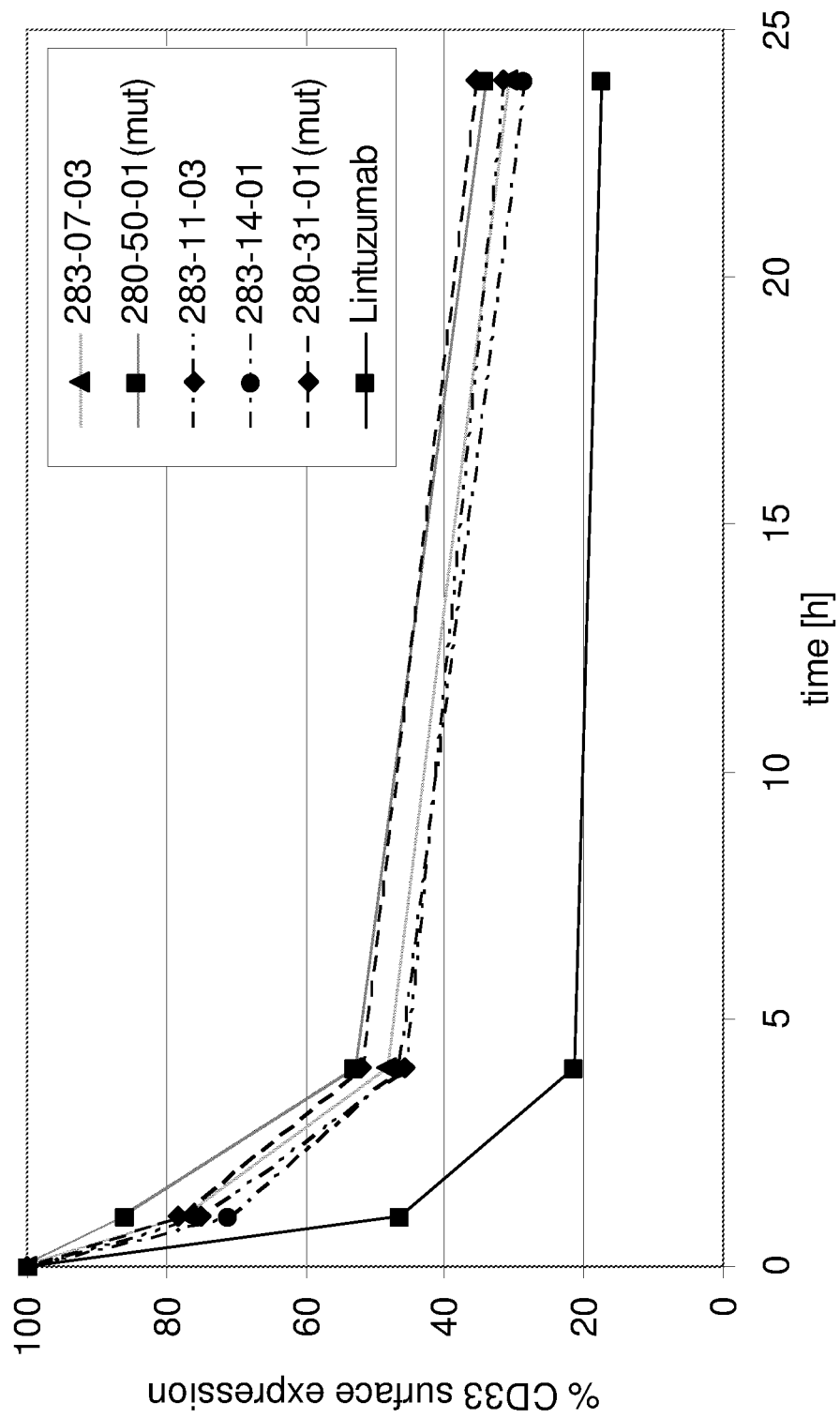

Internalization of antibody refers to the reduction of the amount of antibody/antigen complexes on the cell surface of the target cell after incubation with antibody. Internalization tests were performed with the CD33 expressing HL60 cell line. Cells were incubated with a fixed amount of a CD33 binding agent (10 µg/ml of fully human monoclonal antibodies as listed in table 1 as No. 1-14) for defined time periods (0 h, 1 h, 4 h, 24 h) at 37° C. to allow internalization of the antibody/antigen complex. At the indicated time points acid was added to the incubation mix to prevent further internalization. Thereafter a fixed amount of CD33 binding agent was added to saturate all CD33 antigen sites on the cell surface. The total amount of CD33 binding agent bound to the cell surface was determined by FACS analysis utilizing a FITC conjugated anti-human IgG secondary antibody. The time point 0 h was used to determine the initial level of CD33 antibody/antigen complexes on the surface and was defined as 100%. The results are listed in table 3 and illustrated in FIGS. 1-3.

TABLE 3

| No | Clone ID # | Remaining CD33 antibody/antigen complexes on the cells surface after 4 h incubation with antibody (%) |
|---|---|---|
| 1 | 280-03-08 | 49 |
| 2 | 280-21-09 | 41 |
| 3 | 280-29-12 | 49 |
| 4 | 280-31-01 | 44 |
| 5 | 280-31-01 (mut) | 52 |
| 6 | 280-34-02 | 44 |
| 7 | 280-50-01 | 53 |
| 8 | 280-50-01 (mut) | 55 |
| 9 | 280-61-07 | 47 |
| 10 | 283-03-03 | 45 |
| 11 | 283-05-01 | 51 |
| 12 | 283-07-03 | 48 |
| 13 | 283-11-03 | 46 |
| 14 | 283-14-01 | 47 |

Lintuzumab was included as a reference antibody. Lintuzumab/CD33 complexes rapidly internalized upon binding of lintuzumab which was in accordance to published data. After a 4 h-incubation period only about 20% of the initial amount of CD33/lintuzumab complexes was left on the cell surface. It could be demonstrated that, unexpectedly, internalization of all 14 CD33 binding agents according to the present invention was decelerated compared to lintuzumab.

Example 3: ADCC Activity

Decelerated internalization rate translates into increased ADCC activity in vitro. To assess the effect of decelerated internalization on the ADCC activity of the CD33 binding agents (fully human monoclonal antibodies as listed in table 1 as No. 1-14), target cells (HL60) were incubated with a CD33 binding agent for the 0, 1, 4 and 24 h. Subsequently an ADCC assay was performed with IL-2 stimulated PBMC as effector cells and antibody coated HL60 cells as target cells. For all experiments a mAb concentration of 30 µg/ml used. The co-cultivation of effector cells with target cells in presence of CD33 binding agent was performed in quadruplicates or triplicates in 96-well round-bottom microtiter plates in a final volume of 200 µl assay medium per well consisting of 10% human serum and 1% BSA in RPMI in 1:1 ratio. First effector cells (freshly isolated PBMC cells in 100 µl 10% human serum in RPMI per well) were plated, followed by target cells and CD33 binding agent solution (diluted in 50 µl 1% BSA in RPMI). As a control, effector cells were cultivated in assay medium alone (effector cell control) and target cells were cultivated either in assay medium alone (spontaneous lysis) or in assay medium supplemented with 1% Triton X-100 (maximal lysis). The co-culture was incubated at 37° C. in a humid $CO_2$ incubator for 3 hours. At the end of the incubation cells were removed from the culture medium by centrifugation (200×g, i.e. 1000 rpm; 10 min) at room temperature. Cell free supernatants (100 µl/well) are transferred into corresponding wells of a 96-well flat-bottom plate. To determine the LDH activity in these supernatants 100 µl reaction mixture (freshly mixed 250 µl catalyst with 11.25 ml dye solution) are added to each well and incubated 30 min at room temperature in the dark. Then the absorbance is measured as described below.

Cytotoxicity Detection Kit (LDH; Roche 11 644 793 001) was used to measure ADCC activity. The detection of cytotoxicity is based on the measurement of LDH enzyme activity released from plasma membrane-damaged cells. LDH released into the culture supernatants reduces the tetrazolium salt from the kit to formazan. The absorption maximum of formazan dye is measured at 490 nm against a reference wavelength of 650 nm in an ELISA plate reader. To determine the percentage cell mediated cytotoxicity the average absorbance of the quadruplicates or triplicates was calculated and the background was subtracted. These corrected values were substituted into the following equation to calculate ADCC (%): (effector/target cell mix-effector cell control-spontaneous release) divided by (maximal release-spontaneous release)

ADCC activity at timepoint 0 h (no antibody pre-incubation of target cells) was defined as 100% ADCC activity. ADCC activity for various timepoints of antibody pre-incubation was calculated relative to timepoint 0 h and displayed as relative cytotoxicity (%).

Figure 4:
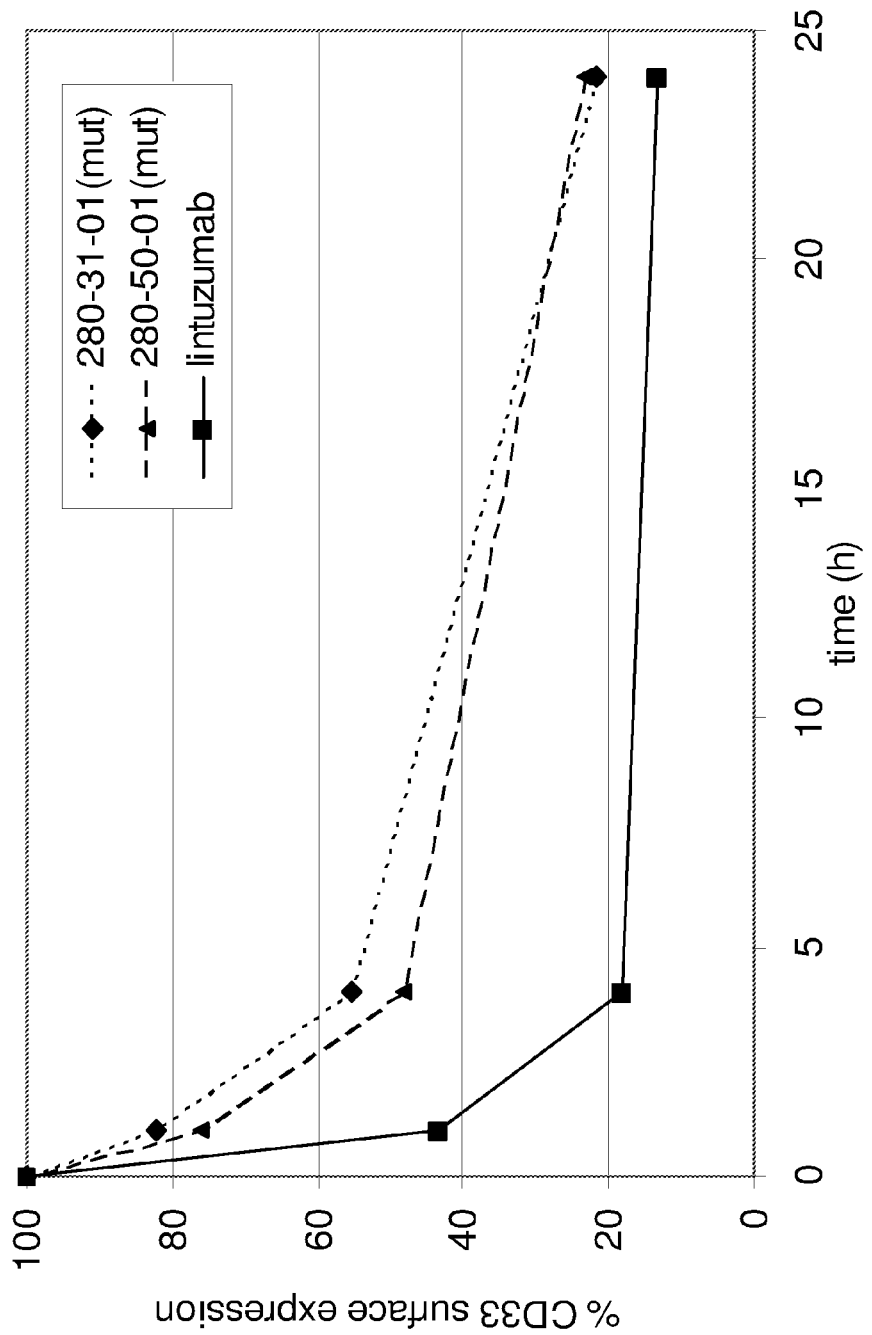
FIG. 4 shows the internalization rate on HL60 cells of two exemplary antibodies according to the invention in comparison to lintuzumab.
Figure 5:
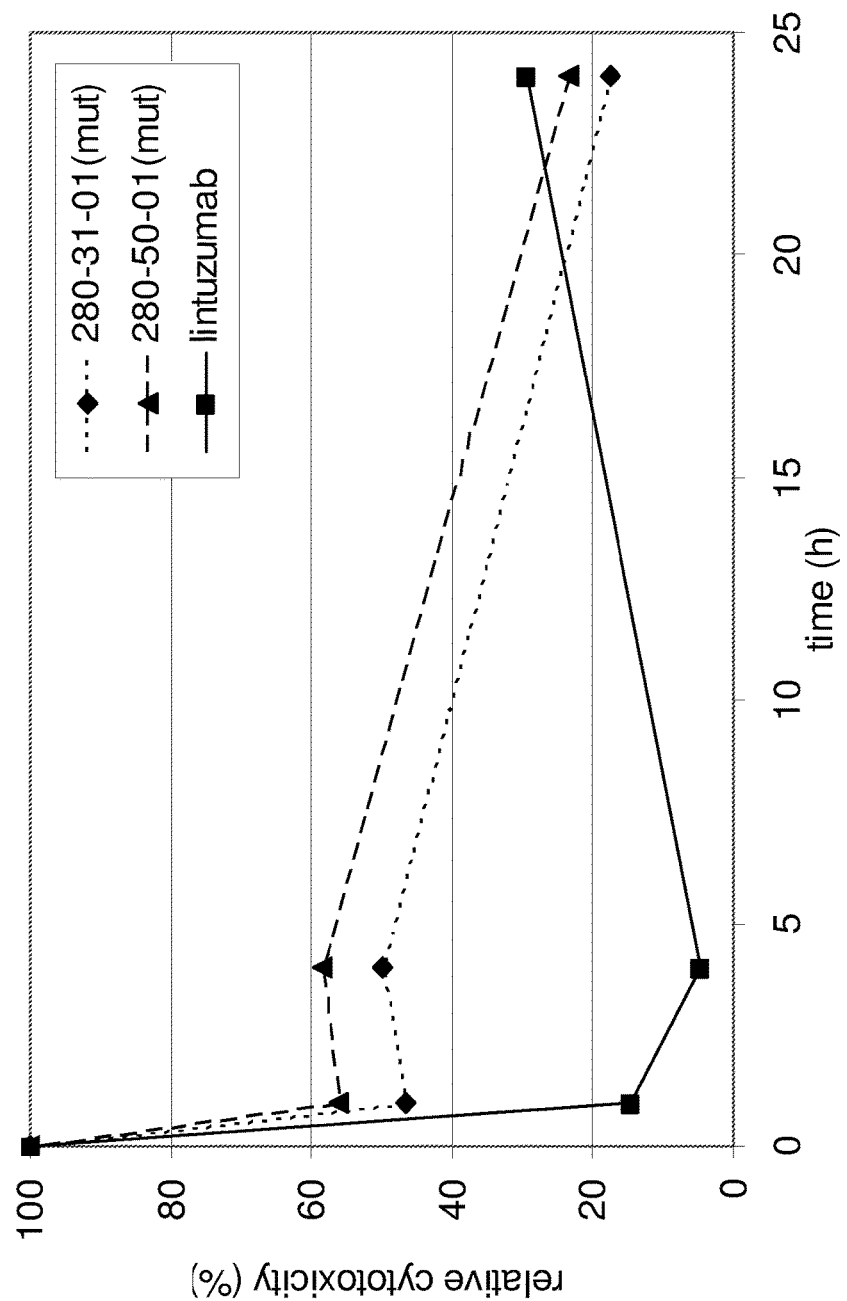
FIG. 5 shows the ADCC performance on HL60 cells of two exemplary antibodies according to the invention in comparison to lintuzumab.

Decelerated internalization of the CD33 binding agents compared to lintuzumab resulted in increased ADCC activity compared to lintuzumab. In conclusion, decelerated internalization leads to increased ADCC activity. Internalization for the described CD33 binding agents is inversely correlated to ADCC activity of the CD33 binding agents which is indicative for advantages with respect to clinical activity of such CD33 binding agents. The results are illustrated in FIG. 4 for the internalization kinetics in this experiment and in FIG. 5 for the ADCC activity.

Example 4: Epitope Mapping

The binding epitope of CD33 binding agents described herein relative to the epitope of lintuzumab was determined by Hydrogen Exchange Mass Spectrometry (HXMS).

This method determined the susceptibility of the amide backbone hydrogens of CD33 protein to exchange with $D_2O$. The experiments were conducted with recombinant CD33 protein alone and CD33 protein with added CD33 binding agent/lintuzumab (in the following in this example referred to as "antibody/antibodies"). Regions of the CD33 protein showing significant protection from exchange due to binding of antibody were thus identified. Resolution of the method is determined by the peptides produced by digestion with pepsin, e.g. the resulting amino acid sequence may be larger than the actual epitope of the antibody. These CD33 derived peptides were identified by additional control experiments with unexchanged samples employing standard accurate mass and HPLC MS/MS technologies.

For the protein+antibody sample, CD33 protein and antibody were incubated for 15 minutes at room temperature. The final molar ratio antibody/CD33 was 2:1. Using a LEAP robot system (exchange plate kept at 25° C., sample/quench plate kept at 4° C.), 8 ul of sample was added to 80 μl of exchange buffer (10 mM $NaH_2PO_4$ in $D_2O$, pH=7 or 10 mM $NaH_2PO_4$ in $H_2O$, pH=7), mixed, and allowed to exchange for various times (15, 60, 120, 240, and 600 seconds) at 25° C. 80 ul of this solution was then transferred to 80 μl of quench buffer (IM urea, 0.1M TCEP-HCl) at 4° C. and mixed. 90 μl of this solution was then transferred to 10 μl of pepsin (4 mg/ml) at 4° C. and mixed. After 2 minutes, 60 μl of this solution was injected onto a Michrom C18 trap cartridge. The cartridge was washed with $H_2O$+0.1% TFA for 2 minutes at 100 μl/min. A valve was then switched and the cartridge eluted onto a Phenomenex Jupiter C5 column, 1.0×50 mm, 5 μm, 300A. Mobile Phase A was water/acetonitrile/TFA (99/0.95/0.05) and Mobile Phase B was acetonitrile/water/TFA (95/4.95/0.05). Flow rate was 100 μl/min. Gradient was: 0 minutes (0% B), 6 minutes (40% B), 7 minutes (40% B), 8 minutes (90% B), 10 minutes (90% B), 11 minutes (0% B). The LEAP system precools the mobile phase to 4° C. and also maintains the trap column and analytical column at 4° C. For the MS experiments (used to quantitate exchange with the $D_2O$ buffer), a single scan method from 300-2000 for 14 minutes was used at resolution 60,000. For the MS/MS experiments (used to ID peptides with the $H_2O$ exchange buffer), a method with 7 scans was used for 14 minutes. The first scan was a full range scan from 300-2000 at 30,000 resolution. Subsequent scans were CID scans of the 6 most intense ions from scan #1. Isolation width was 1.5 amu, collision energy was 35V, activation time was 30 msec. Pepsin peptides were identified using fragmentation data and the program Proteome Discoverer (Thermo). Identified peptides were analyzed using an in-house program which calculates the average mass for exchanged peptides.

All CD33 binding agents protected the identical peptide fragment with the amino acid sequence FFHPIPYYD-KNSPVHGYW (Seq ID No: 141) (Table 4). The sequence of CD33 protected by the CD33 binding agents described herein are different and non-overlapping to the peptide sequence of CD33 protected by binding of Lintuzumab (MDPNFWLQVQE, Seq ID No: 142). In silico modeling using the crystal structure of SIGLEC-5, a SIGLEC family member homologous to CD33, revealed binding epitopes of all antibodies in the proximal domain of the protein, where the binding epitope of Lintuzumab is different to those of the CD33 binding agents described herein. In conclusion, the CD33 binding agents described in this patent application bind to a different epitope than Lintuzumab.

TABLE 4

| No | Clone ID # | CD33 Epitope |
|---|---|---|
| 1 | 280-03-08 | FFHPIPYYDKNSPVHGYW |
| 2 | 280-21-09 | FFHPIPYYDKNSPVHGYW |
| 3 | 280-29-12 | FFHPIPYYDKNSPVHGYW |
| 4 | 280-31-01 | FFHPIPYYDKNSPVHGYW |
| 5 | 280-31-01 (mut) | FFHPIPYYDKNSPVHGYW |
| 6 | 280-34-02 | FFHPIPYYDKNSPVHGYW |
| 7 | 280-50-01 | FFHPIPYYDKNSPVHGYW |
| 8 | 280-50-01 (mut) | FFHPIPYYDKNSPVHGYW |
| 9 | 280-61-07 | FFHPIPYYDKNSPVHGYW |
| 10 | 283-03-03 | FFHPIPYYDKNSPVHGYW |
| 11 | 283-05-01 | FFHPIPYYDKNSPVHGYW |
| 12 | 283-07-03 | FFHPIPYYDKNSPVHGYW |
| 13 | 283-11-03 | FFHPIPYYDKNSPVHGYW |
| 14 | 283-14-01 | FFHPIPYYDKNSPVHGYW |
| 15 | Lintuzumab | MDPNFWLQVQE |

The invention claimed is:

1. A method of depleting CD33 expressing myeloid cells in a patient, comprising administering to said patient
   a) one or more CD33 binding agents being defined by having a heavy chain variable region comprising CDR1, CDR2 and CDR3, and a light chain variable region comprising CDR4, CDR5 and CDR6, wherein CDR1 has an amino acid sequence selected from Seq ID No:29-42, CDR2 has an amino acid sequence selected from Seq ID No:15-28, CDR3 has an amino acid sequence selected from Seq ID No:1-14, CDR4 has an amino acid sequence selected from Seq ID No:71-84, CDR5 has an amino acid sequence selected from Seq ID No: 57-70, CDR6 has an amino acid sequence selected from Seq ID No:43-56, or
   b) a pharmaceutical composition comprising said one or more CD33 binding agents.

2. A method of depleting CD33 expressing myeloid cells in a patient, comprising administering to said patient one or more CD33 binding agents selected from an antibody comprising a CDR1 of Seq ID No: 29, a CDR2 of Seq ID No: 15, a CDR3 of Seq ID No: 1, a CDR4 of Seq ID No: 71, a CDR5 of Seq ID No: 57 and a CDR6 of Seq ID No: 43, an antibody comprising a CDR1 of Seq ID No: 30, a CDR2 of Seq ID No: 16, a CDR3 of Seq ID No: 2, a CDR4 of Seq ID No: 72, a CDR5 of Seq ID No: 58 and a CDR6 of Seq ID No: 44, an antibody comprising a CDR1 of Seq ID No: 31, a CDR2 of Seq ID No: 17, a CDR3 of Seq ID No: 3, a CDR4 of Seq ID No: 73, a CDR5 of Seq ID No: 59 and a CDR6 of Seq ID No: 45, an antibody comprising a CDR1 of Seq ID No: 32, a CDR2 of Seq ID No: 18, a CDR3 of Seq ID No: 4, a CDR4 of Seq ID No: 74, a CDR5 of Seq ID No: 60 and a CDR6 of Seq ID No: 46, an antibody comprising a CDR1 of Seq ID No: 33, a CDR2 of Seq ID No: 19, a CDR3 of Seq ID No: 5, a CDR4 of Seq ID No: 75, a CDR5 of Seq ID No: 61 and a CDR6 of Seq ID No: 47, an antibody comprising a CDR1 of Seq ID No: 34, a CDR2 of Seq ID No: 20, a CDR3 of Seq ID No: 6, a CDR4 of Seq ID No: 76, a CDR5 of Seq ID No: 62 and a CDR6 of Seq ID No: 48, an antibody comprising a CDR1 of Seq ID No: 35, a CDR2 of Seq ID No: 21, a CDR3 of Seq ID No: 7, a CDR4 of Seq ID No: 77, a CDR5 of Seq ID No: 63 and a CDR6 of Seq ID No: 49, an antibody comprising a CDR1 of Seq ID No: 36, a CDR2 of Seq ID No: 22, a CDR3 of Seq ID No: 8, a CDR4 of Seq ID No: 78, a CDR5 of Seq ID No: 64 and a CDR6 of Seq ID No: 50, an antibody comprising a CDR1 of Seq ID No: 37, a CDR2 of Seq ID No: 23, a CDR3 of Seq ID No: 9, a CDR4 of Seq ID No: 79, a CDR5 of Seq ID No: 65 and a CDR6 of Seq ID No: 51, an antibody comprising a CDR1 of Seq ID No: 38, a CDR2 of Seq ID No: 24, a CDR3 of Seq ID No: 10, a CDR4 of Seq ID No: 80, a CDR5 of Seq ID No: 66 and a CDR6 of Seq ID No: 52, an antibody comprising a CDR1 of Seq ID No: 39, a CDR2 of Seq ID No: 25, a CDR3 of Seq ID No: 11, a CDR4 of Seq ID No: 81 a CDR5 of Seq ID No: 67 and a CDR6 of Seq ID No: 53, an antibody comprising a CDR1 of Seq ID No: 40, a CDR2 of Seq ID No: 26, a CDR3 of Seq ID No: 12, a CDR4 of Seq ID No: 82, a CDR5 of Seq ID No: 68 and a CDR6 of Seq ID No: 54, an antibody comprising a CDR1 of Seq ID No: 41, a CDR2 of Seq ID No: 27, a CDR3 of Seq ID No: 13, a CDR4 of Seq ID No: 83, a CDR5 of Seq ID No: 69 and a CDR6 of Seq ID No: 55, or an antibody comprising a CDR1 of Seq ID No: 42, a CDR2 of Seq ID No: 28, a CDR3 of Seq ID No: 14, a CDR4 of Seq ID No: 84, a CDR5 of Seq ID No: 70 and a CDR6 of Seq ID No: 56, or a pharmaceutical composition comprising said one or more CD33 binding agents.

3. A method of depleting CD33 expressing myeloid cells in a patient, comprising administering to said patient one or more CD33 binding agents selected from an antibody comprising a heavy chain variable region of Seq ID No: 85 and a light chain variable region of Seq ID No: 99, an antibody comprising a heavy chain variable region of Seq ID No: 86 and a light chain variable region of Seq ID No: 100, an antibody comprising a heavy chain variable region of Seq ID No: 87 and a light chain variable region of Seq ID No: 101, an antibody comprising a heavy chain variable region of Seq ID No: 88 and a light chain variable region of Seq ID No: 102, an antibody comprising a heavy chain variable region of Seq ID No: 89 and a light chain variable region of Seq ID No: 103, an antibody comprising a heavy chain variable region of Seq ID No: 90 and a light chain variable region of Seq ID No: 104, an antibody comprising a heavy chain variable region of Seq ID No: 91 and a light chain variable region of Seq ID No: 105, an antibody comprising a heavy chain variable region of Seq ID No: 92 and a light chain variable region of Seq ID No: 106, an antibody comprising a heavy chain variable region of Seq ID No: 93 and a light chain variable region of Seq ID No: 107, an antibody comprising a heavy chain variable region of Seq ID No: 94 and a light chain variable region of Seq ID No: 108, an antibody comprising a heavy chain variable region of Seq ID No: 95 and a light chain variable region of Seq ID No: 109, an antibody comprising a heavy chain variable region of Seq ID No: 96 and a light chain variable region of Seq ID No: 110, an antibody comprising a heavy chain variable region of Seq ID No: 97 and a light chain variable region of Seq ID No: 111, an antibody comprising a heavy chain variable region of Seq ID No: 98 and a light chain variable region of Seq ID No: 112, an antibody comprising a heavy chain of Seq ID No: 113 and a light chain of Seq ID No: 127, an antibody comprising a heavy chain of Seq ID No: 114 and a light chain of Seq ID No: 128, an antibody comprising a heavy chain of Seq ID No: 115 and a light chain of Seq ID No: 129, an antibody comprising a heavy chain of Seq ID No: 116 and a light chain of Seq ID No: 130, an antibody comprising a heavy chain of Seq ID No: 117 and a light chain of Seq ID No: 131, an antibody comprising a heavy chain of Seq ID No: 118 and a light chain of Seq ID No: 132, an antibody comprising a heavy chain of Seq ID No: 119 and a light chain of Seq ID No: 133, an antibody comprising a heavy chain of Seq ID No: 120 and a light chain of Seq ID No: 134, an antibody comprising a heavy chain of Seq ID No: 121 and a light chain of Seq ID No: 135, an antibody comprising a heavy chain of Seq ID No: 122 and a light chain of Seq ID No: 136, an antibody comprising a heavy chain of Seq ID No: 123 and a light chain of Seq ID No: 137, an antibody comprising a heavy chain of Seq ID No: 124 and a light chain of Seq ID No: 138, an antibody comprising a heavy chain of Seq ID No: 125 and a light chain of Seq ID No: 139, or an antibody comprising a heavy chain of Seq ID No: 126 and a light chain of Seq ID No: 140, or a pharmaceutical composition comprising said one or more CD33 binding agents.

4. A method of depleting CD33 expressing myeloid cells in a patient, comprising administering to said patient one or more CD33 binding agents selected from a) an antibody comprising a CDR1 of Seq ID No: 29, a CDR2 of Seq ID No: 15, a CDR3 of Seq ID No: 1, a CDR4 of Seq ID No: 71, a CDR5 of Seq ID No: 57 and a CDR6 of Seq ID No: 43, or a pharmaceutical composition thereof;

b) an antibody comprising a heavy chain variable region of Seq ID No: 85 and a light chain variable region of Seq ID No: 99, or a pharmaceutical composition thereof; or c) an antibody comprising a heavy chain of Seq ID No: 113 and a light chain of Seq ID No: 127, or a pharmaceutical composition thereof.

5. A method of depleting CD33 expressing myeloid cells in a patient, comprising administering to said patient one or more CD33 binding agents selected from a) an antibody comprising a CDR1 of Seq ID No: 30, a CDR2 of Seq ID No: 16, a CDR3 of Seq ID No: 2, a CDR4 of Seq ID No: 72, a CDR5 of Seq ID No: 58 and a CDR6 of Seq ID No: 44, or a pharmaceutical composition thereof;

b) an antibody comprising a heavy chain variable region of Seq ID No: 86 and a light chain variable region of Seq ID No: 100, or a pharmaceutical composition thereof; or c) an antibody comprising a heavy chain of Seq ID No: 114 and a light chain of Seq ID No: 128, or a pharmaceutical composition thereof.

6. A method of depleting CD33 expressing myeloid cells in a patient, comprising administering to said patient one or more CD33 binding agents selected from
   a) an antibody comprising a CDR1 of Seq ID No: 31, a CDR2 of Seq ID No: 17, a CDR3 of Seq ID No: 3, a CDR4 of Seq ID No: 73, a CDR5 of Seq ID No: 59 and a CDR6 of Seq ID No: 45, or a pharmaceutical composition thereof;
   b) an antibody comprising a heavy chain variable region of Seq ID No: 87 and a light chain variable region of Seq ID No: 101, or a pharmaceutical composition thereof; or
   c) an antibody comprising a heavy chain of Seq ID No: 115 and a light chain of Seq ID No: 129, or a pharmaceutical composition thereof.

7. A method of depleting CD33 expressing myeloid cells in a patient, comprising administering to said patient one or more CD33 binding agents selected from
   a) an antibody comprising a CDR1 of Seq ID No: 32, a CDR2 of Seq ID No: 18, a CDR3 of Seq ID No: 4, a CDR4 of Seq ID No: 74, a CDR5 of Seq ID No: 60 and a CDR6 of Seq ID No: 46, or a pharmaceutical composition thereof;
   b) an antibody comprising a heavy chain variable region of Seq ID No: 88 and a light chain variable region of Seq ID No: 102, or a pharmaceutical composition thereof; or
   c) an antibody comprising a heavy chain of Seq ID No: 116 and a light chain of Seq ID No: 130, or a pharmaceutical composition thereof.

8. A method of depleting CD33 expressing myeloid cells in a patient, comprising administering to said patient one or more CD33 binding agents selected from
   a) an antibody comprising a CDR1 of Seq ID No: 33, a CDR2 of Seq ID No: 19, a CDR3 of Seq ID No: 5, a CDR4 of Seq ID No: 75, a CDR5 of Seq ID No: 61 and a CDR6 of Seq ID No: 47, or a pharmaceutical composition thereof;
   b) an antibody comprising a heavy chain variable region of Seq ID No: 89 and a light chain variable region of Seq ID No: 103, or a pharmaceutical composition thereof; or
   c) an antibody comprising a heavy chain of Seq ID No: 117 and a light chain of Seq ID No: 131, or a pharmaceutical composition thereof.

9. A method of depleting CD33 expressing myeloid cells in a patient, comprising administering to said patient one or more CD33 binding agents selected from
   a) an antibody comprising a CDR1 of Seq ID No: 34, a CDR2 of Seq ID No: 20, a CDR3 of Seq ID No: 6, a CDR4 of Seq ID No: 76, a CDR5 of Seq ID No: 62 and a CDR6 of Seq ID No: 48, or a pharmaceutical composition thereof;
   b) an antibody comprising a heavy chain variable region of Seq ID No: 90 and a light chain variable region of Seq ID No: 104, or a pharmaceutical composition thereof; or
   c) an antibody comprising a heavy chain of Seq ID No: 118 and a light chain of Seq ID No: 132, or a pharmaceutical composition thereof.

10. A method of depleting CD33 expressing myeloid cells in a patient, comprising administering to said patient one or more CD33 binding agents selected from
    a) an antibody comprising a CDR1 of Seq ID No: 35, a CDR2 of Seq ID No: 21, a CDR3 of Seq ID No: 7, a CDR4 of Seq ID No: 77, a CDR5 of Seq ID No: 63 and a CDR6 of Seq ID No: 49, or a pharmaceutical composition thereof;
    b) an antibody comprising a heavy chain variable region of Seq ID No: 91 and a light chain variable region of Seq ID No: 105, or a pharmaceutical composition thereof; or
    c) an antibody comprising a heavy chain of Seq ID No: 119 and a light chain of Seq ID No: 133, or a pharmaceutical composition thereof.

11. A method of depleting CD33 expressing myeloid cells in a patient, comprising administering to said patient one or more CD33 binding agents selected from
    a) an antibody comprising a CDR1 of Seq ID No: 36, a CDR2 of Seq ID No: 22, a CDR3 of Seq ID No: 8, a CDR4 of Seq ID No: 78, a CDR5 of Seq ID No: 64 and a CDR6 of Seq ID No: 50, or a pharmaceutical composition thereof;
    b) an antibody comprising a heavy chain variable region of Seq ID No: 92 and a light chain variable region of Seq ID No: 106, or a pharmaceutical composition thereof; or
    c) an antibody comprising a heavy chain of Seq ID No: 120 and a light chain of Seq ID No: 134, or a pharmaceutical composition thereof.

12. A method of depleting CD33 expressing myeloid cells in a patient, comprising administering to said patient one or more CD33 binding agents selected from
    a) an antibody comprising a CDR1 of Seq ID No: 37, a CDR2 of Seq ID No: 23, a CDR3 of Seq ID No: 9, a CDR4 of Seq ID No: 79, a CDR5 of Seq ID No: 65 and a CDR6 of Seq ID No: 51, or a pharmaceutical composition thereof;
    b) an antibody comprising a heavy chain variable region of Seq ID No: 93 and a light chain variable region of Seq ID No: 107, or a pharmaceutical composition thereof; or
    c) an antibody comprising a heavy chain of Seq ID No: 121 and a light chain of Seq ID No: 135, or a pharmaceutical composition thereof.

* * * * *

SEQUENCE LISTING

```
<160> NUMBER OF SEQ ID NOS: 140

<210> SEQ ID NO 1
<211> LENGTH: 8
<212> TYPE: PRT
<213> ORGANISM: Artificial
<220> FEATURE:
<223> OTHER INFORMATION: CDR

<400> SEQUENCE: 1
```

Asn Trp Ala Asp Ala Phe Asp Ile
1               5

<210> SEQ ID NO 2
<211> LENGTH: 8
<212> TYPE: PRT
<213> ORGANISM: Artificial
<220> FEATURE:
<223> OTHER INFORMATION: CDR

<400> SEQUENCE: 2

Asn Trp Ala Asp Ala Phe Asp Ile
1               5

<210> SEQ ID NO 3
<211> LENGTH: 8
<212> TYPE: PRT
<213> ORGANISM: Artificial
<220> FEATURE:
<223> OTHER INFORMATION: CDR

<400> SEQUENCE: 3

His Trp Leu Asp Ala Phe Asp Ile
1               5

<210> SEQ ID NO 4
<211> LENGTH: 8
<212> TYPE: PRT
<213> ORGANISM: Artificial
<220> FEATURE:
<223> OTHER INFORMATION: CDR

<400> SEQUENCE: 4

Asn Trp Ala Asp Ala Phe Asp Ile
1               5

<210> SEQ ID NO 5
<211> LENGTH: 8
<212> TYPE: PRT
<213> ORGANISM: Artificial
<220> FEATURE:
<223> OTHER INFORMATION: CDR

<400> SEQUENCE: 5

Asn Trp Ala Asp Ala Phe Asp Ile
1               5

<210> SEQ ID NO 6
<211> LENGTH: 8
<212> TYPE: PRT
<213> ORGANISM: Artificial
<220> FEATURE:
<223> OTHER INFORMATION: CDR

<400> SEQUENCE: 6

Asn Trp Ala Asp Ala Phe Asp Ile
1               5

<210> SEQ ID NO 7
<211> LENGTH: 8
<212> TYPE: PRT
<213> ORGANISM: Artificial
<220> FEATURE:
<223> OTHER INFORMATION: CDR

<400> SEQUENCE: 7

Asn Trp Ala Asp Ala Phe Asp Ile

```
1               5

<210> SEQ ID NO 8
<211> LENGTH: 19
<212> TYPE: PRT
<213> ORGANISM: Artificial
<220> FEATURE:
<223> OTHER INFORMATION: CDR

<400> SEQUENCE: 8

Asn Trp Ala Asp Ala Phe Asp Ile Trp Gly Gln Gly Thr Met Val Thr
1               5                   10                  15

Val Ser Ser

<210> SEQ ID NO 9
<211> LENGTH: 19
<212> TYPE: PRT
<213> ORGANISM: Artificial
<220> FEATURE:
<223> OTHER INFORMATION: CDR

<400> SEQUENCE: 9

Asn Trp Ala Asp Ala Phe Asp Ile Trp Gly Gln Gly Thr Met Val Thr
1               5                   10                  15

Val Ser Ser

<210> SEQ ID NO 10
<211> LENGTH: 10
<212> TYPE: PRT
<213> ORGANISM: Artificial
<220> FEATURE:
<223> OTHER INFORMATION: CDR

<400> SEQUENCE: 10

Glu Gly Gly Val Asp Trp Tyr Phe Asp Leu
1               5                   10

<210> SEQ ID NO 11
<211> LENGTH: 10
<212> TYPE: PRT
<213> ORGANISM: Artificial
<220> FEATURE:
<223> OTHER INFORMATION: CDR

<400> SEQUENCE: 11

Glu Gly Gly Val Asp Trp Tyr Phe Asp Leu
1               5                   10

<210> SEQ ID NO 12
<211> LENGTH: 10
<212> TYPE: PRT
<213> ORGANISM: Artificial
<220> FEATURE:
<223> OTHER INFORMATION: CDR

<400> SEQUENCE: 12

Glu Gly Gly Val Asp Trp Tyr Phe Asp Leu
1               5                   10

<210> SEQ ID NO 13
<211> LENGTH: 10
<212> TYPE: PRT
<213> ORGANISM: Artificial
<220> FEATURE:
<223> OTHER INFORMATION: CDR
```

```
<400> SEQUENCE: 13

Glu Gly Gly Val Asp Trp Tyr Phe Asp Leu
1               5                   10

<210> SEQ ID NO 14
<211> LENGTH: 10
<212> TYPE: PRT
<213> ORGANISM: Artificial
<220> FEATURE:
<223> OTHER INFORMATION: CDR

<400> SEQUENCE: 14

Glu Gly Gly Val Asp Trp Tyr Phe Asp Leu
1               5                   10

<210> SEQ ID NO 15
<211> LENGTH: 17
<212> TYPE: PRT
<213> ORGANISM: Artificial
<220> FEATURE:
<223> OTHER INFORMATION: CDR

<400> SEQUENCE: 15

Arg Ile Ile Pro Ile Leu Gly Val Ala Asn Tyr Ala Gln Lys Phe Gln
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: CDR

<400> SEQUENCE: 16

Arg Ile Ile Pro Ile Ile Asn Ile Ala Ser Tyr Ala Gln Asn Phe Gln
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: CDR

<400> SEQUENCE: 17

Arg Ile Ile Pro Ile Ile Gly Ile Ala Asn Tyr Ala Gln Lys Phe Gln
1               5                   10                  15

Gly

<210> SEQ ID NO 18
<211> LENGTH: 17
<212> TYPE: PRT
<213> ORGANISM: Artificial
<220> FEATURE:
<223> OTHER INFORMATION: CDR

<400> SEQUENCE: 18

Arg Ile Ile Pro Ile Leu Gly Val Ala Asp Tyr Ala Gln Lys Phe Gln
1               5                   10                  15

Gly
```

-continued

```
<210> SEQ ID NO 19
<211> LENGTH: 17
<212> TYPE: PRT
<213> ORGANISM: Artificial
<220> FEATURE:
<223> OTHER INFORMATION: CDR

<400> SEQUENCE: 19

Arg Ile Ile Pro Ile Leu Gly Val Ala Asp Tyr Ala Gln Lys Phe Gln
1               5                   10                  15

Gly

<210> SEQ ID NO 20
<211> LENGTH: 17
<212> TYPE: PRT
<213> ORGANISM: Artificial
<220> FEATURE:
<223> OTHER INFORMATION: CDR

<400> SEQUENCE: 20

Arg Ile Ile Pro Ile Val Gly Ile Val Asn Tyr Ala Glu Lys Phe Gln
1               5                   10                  15

Gly

<210> SEQ ID NO 21
<211> LENGTH: 17
<212> TYPE: PRT
<213> ORGANISM: Artificial
<220> FEATURE:
<223> OTHER INFORMATION: CDR

<400> SEQUENCE: 21

Arg Val Ile Pro Ile Ile Gly Ile Ala Ser Tyr Ala Gln Asn Phe Gln
1               5                   10                  15

Gly

<210> SEQ ID NO 22
<211> LENGTH: 17
<212> TYPE: PRT
<213> ORGANISM: Artificial
<220> FEATURE:
<223> OTHER INFORMATION: CDR

<400> SEQUENCE: 22

Arg Val Ile Pro Ile Ile Gly Ile Ala Ser Tyr Ala Gln Asn Phe Gln
1               5                   10                  15

Gly

<210> SEQ ID NO 23
<211> LENGTH: 17
<212> TYPE: PRT
<213> ORGANISM: Artificial
<220> FEATURE:
<223> OTHER INFORMATION: CDR

<400> SEQUENCE: 23

Arg Val Ile Pro Ile Ile Gly Ile Ala Ser Tyr Ala Gln Asn Phe Glu
1               5                   10                  15

Gly

<210> SEQ ID NO 24
<211> LENGTH: 17
<212> TYPE: PRT
<213> ORGANISM: Artificial
```

<220> FEATURE:
<223> OTHER INFORMATION: CDR

<400> SEQUENCE: 24

Arg Ile Ile Pro Ile Leu Asp Met Ala Asn Tyr Ala Gln Lys Phe Gln
1               5                   10                  15

Gly

<210> SEQ ID NO 25
<211> LENGTH: 17
<212> TYPE: PRT
<213> ORGANISM: Artificial
<220> FEATURE:
<223> OTHER INFORMATION: CDR

<400> SEQUENCE: 25

Arg Ile Ile Pro Ile Ile Gly Ile Val Asn Tyr Ala Gln Lys Phe Gln
1               5                   10                  15

Gly

<210> SEQ ID NO 26
<211> LENGTH: 17
<212> TYPE: PRT
<213> ORGANISM: Artificial
<220> FEATURE:
<223> OTHER INFORMATION: CDR

<400> SEQUENCE: 26

Arg Ile Ile Pro Ile Leu Gly Met Ala Asn Tyr Ala Gln Lys Phe Gln
1               5                   10                  15

Gly

<210> SEQ ID NO 27
<211> LENGTH: 17
<212> TYPE: PRT
<213> ORGANISM: Artificial
<220> FEATURE:
<223> OTHER INFORMATION: CDR

<400> SEQUENCE: 27

Arg Ile Ile Pro Ile Ile Gly Ile Val Asn Tyr Ala Gln Lys Phe Gln
1               5                   10                  15

Gly

<210> SEQ ID NO 28
<211> LENGTH: 17
<212> TYPE: PRT
<213> ORGANISM: Artificial
<220> FEATURE:
<223> OTHER INFORMATION: CDR

<400> SEQUENCE: 28

Arg Ile Ile Pro Ile Leu Gly Ile Ala Asn Tyr Ala Gln Lys Phe Gln
1               5                   10                  15

Gly

<210> SEQ ID NO 29
<211> LENGTH: 5
<212> TYPE: PRT
<213> ORGANISM: Artificial
<220> FEATURE:
<223> OTHER INFORMATION: CDR

<400> SEQUENCE: 29

```
Asp Tyr Ala Ile Ser
1               5

<210> SEQ ID NO 30
<211> LENGTH: 5
<212> TYPE: PRT
<213> ORGANISM: Artificial
<220> FEATURE:
<223> OTHER INFORMATION: CDR

<400> SEQUENCE: 30

Ser Tyr Ala Ile Ser
1               5

<210> SEQ ID NO 31
<211> LENGTH: 5
<212> TYPE: PRT
<213> ORGANISM: Artificial
<220> FEATURE:
<223> OTHER INFORMATION: CDR

<400> SEQUENCE: 31

Ser Tyr Ala Ile Ser
1               5

<210> SEQ ID NO 32
<211> LENGTH: 5
<212> TYPE: PRT
<213> ORGANISM: Artificial
<220> FEATURE:
<223> OTHER INFORMATION: CDR

<400> SEQUENCE: 32

Asp Tyr Ala Ile Ser
1               5

<210> SEQ ID NO 33
<211> LENGTH: 5
<212> TYPE: PRT
<213> ORGANISM: Artificial
<220> FEATURE:
<223> OTHER INFORMATION: CDR

<400> SEQUENCE: 33

Asp Tyr Ala Ile Ser
1               5

<210> SEQ ID NO 34
<211> LENGTH: 5
<212> TYPE: PRT
<213> ORGANISM: Artificial
<220> FEATURE:
<223> OTHER INFORMATION: CDR

<400> SEQUENCE: 34

Ser Tyr Ala Ile Ser
1               5

<210> SEQ ID NO 35
<211> LENGTH: 5
<212> TYPE: PRT
<213> ORGANISM: Artificial
<220> FEATURE:
<223> OTHER INFORMATION: CDR

<400> SEQUENCE: 35
```

Ser Tyr Ala Ile Ser
1               5

<210> SEQ ID NO 36
<211> LENGTH: 5
<212> TYPE: PRT
<213> ORGANISM: Artificial
<220> FEATURE:
<223> OTHER INFORMATION: CDR

<400> SEQUENCE: 36

Ser Tyr Ala Ile Ser
1               5

<210> SEQ ID NO 37
<211> LENGTH: 5
<212> TYPE: PRT
<213> ORGANISM: Artificial
<220> FEATURE:
<223> OTHER INFORMATION: CDR

<400> SEQUENCE: 37

Ser Tyr Ala Ile Ser
1               5

<210> SEQ ID NO 38
<211> LENGTH: 5
<212> TYPE: PRT
<213> ORGANISM: Artificial
<220> FEATURE:
<223> OTHER INFORMATION: CDR

<400> SEQUENCE: 38

Ser Tyr Ala Ile Ser
1               5

<210> SEQ ID NO 39
<211> LENGTH: 5
<212> TYPE: PRT
<213> ORGANISM: Artificial
<220> FEATURE:
<223> OTHER INFORMATION: CDR

<400> SEQUENCE: 39

Ser Tyr Ala Ile Ser
1               5

<210> SEQ ID NO 40
<211> LENGTH: 5
<212> TYPE: PRT
<213> ORGANISM: Artificial
<220> FEATURE:
<223> OTHER INFORMATION: CDR

<400> SEQUENCE: 40

Ser Tyr Ala Ile Ser
1               5

<210> SEQ ID NO 41
<211> LENGTH: 5
<212> TYPE: PRT
<213> ORGANISM: Artificial
<220> FEATURE:
<223> OTHER INFORMATION: CDR

<400> SEQUENCE: 41

Ser Tyr Ala Ile Ser

```
1               5

<210> SEQ ID NO 42
<211> LENGTH: 5
<212> TYPE: PRT
<213> ORGANISM: Artificial
<220> FEATURE:
<223> OTHER INFORMATION: CDR

<400> SEQUENCE: 42

Ser Tyr Ala Ile Ser
1               5

<210> SEQ ID NO 43
<211> LENGTH: 8
<212> TYPE: PRT
<213> ORGANISM: Artificial
<220> FEATURE:
<223> OTHER INFORMATION: CDR

<400> SEQUENCE: 43

Gln Gln Phe Asn Ser Ser Ile Thr
1               5

<210> SEQ ID NO 44
<211> LENGTH: 8
<212> TYPE: PRT
<213> ORGANISM: Artificial
<220> FEATURE:
<223> OTHER INFORMATION: CDR

<400> SEQUENCE: 44

Gln Gln Phe Asn Ser Ser Ile Thr
1               5

<210> SEQ ID NO 45
<211> LENGTH: 8
<212> TYPE: PRT
<213> ORGANISM: Artificial
<220> FEATURE:
<223> OTHER INFORMATION: CDR

<400> SEQUENCE: 45

Gln Gln Phe Asn Ser Ser Ile Thr
1               5

<210> SEQ ID NO 46
<211> LENGTH: 8
<212> TYPE: PRT
<213> ORGANISM: Artificial
<220> FEATURE:
<223> OTHER INFORMATION: CDR

<400> SEQUENCE: 46

Gln Gln Phe Asn Ser Ser Ile Thr
1               5

<210> SEQ ID NO 47
<211> LENGTH: 8
<212> TYPE: PRT
<213> ORGANISM: Artificial
<220> FEATURE:
<223> OTHER INFORMATION: CDR

<400> SEQUENCE: 47

Gln Gln Phe Asp Ser Ser Ile Thr
1               5
```

```
<210> SEQ ID NO 48
<211> LENGTH: 8
<212> TYPE: PRT
<213> ORGANISM: Artificial
<220> FEATURE:
<223> OTHER INFORMATION: CDR

<400> SEQUENCE: 48

Gln Gln Phe Asn Ser Ser Tyr Thr
1               5

<210> SEQ ID NO 49
<211> LENGTH: 8
<212> TYPE: PRT
<213> ORGANISM: Artificial
<220> FEATURE:
<223> OTHER INFORMATION: CDR

<400> SEQUENCE: 49

Gln Gln Phe Asn Ser Ser Ile Thr
1               5

<210> SEQ ID NO 50
<211> LENGTH: 8
<212> TYPE: PRT
<213> ORGANISM: Artificial
<220> FEATURE:
<223> OTHER INFORMATION: CDR

<400> SEQUENCE: 50

Gln Gln Phe Asp Ser Ser Ile Thr
1               5

<210> SEQ ID NO 51
<211> LENGTH: 8
<212> TYPE: PRT
<213> ORGANISM: Artificial
<220> FEATURE:
<223> OTHER INFORMATION: CDR

<400> SEQUENCE: 51

Gln Gln Phe Asn Ser Ser Ile Thr
1               5

<210> SEQ ID NO 52
<211> LENGTH: 8
<212> TYPE: PRT
<213> ORGANISM: Artificial
<220> FEATURE:
<223> OTHER INFORMATION: CDR

<400> SEQUENCE: 52

Gln Gln Phe Asn Ser Ser Ile Thr
1               5

<210> SEQ ID NO 53
<211> LENGTH: 8
<212> TYPE: PRT
<213> ORGANISM: Artificial
<220> FEATURE:
<223> OTHER INFORMATION: CDR

<400> SEQUENCE: 53

Gln Gln Phe Asn Ser Ser Ile Thr
1               5
```

```
<210> SEQ ID NO 54
<211> LENGTH: 8
<212> TYPE: PRT
<213> ORGANISM: Artificial
<220> FEATURE:
<223> OTHER INFORMATION: CDR

<400> SEQUENCE: 54

Gln Gln Phe Asn Ser Ser Ile Thr
1               5

<210> SEQ ID NO 55
<211> LENGTH: 8
<212> TYPE: PRT
<213> ORGANISM: Artificial
<220> FEATURE:
<223> OTHER INFORMATION: CDR

<400> SEQUENCE: 55

Gln Gln Phe Asn Ser Ser Ile Thr
1               5

<210> SEQ ID NO 56
<211> LENGTH: 8
<212> TYPE: PRT
<213> ORGANISM: Artificial
<220> FEATURE:
<223> OTHER INFORMATION: CDR

<400> SEQUENCE: 56

Gln Gln Phe Asn Ser Ser Ile Thr
1               5

<210> SEQ ID NO 57
<211> LENGTH: 7
<212> TYPE: PRT
<213> ORGANISM: Artificial
<220> FEATURE:
<223> OTHER INFORMATION: CDR

<400> SEQUENCE: 57

Asp Ala Ser Ser Leu Glu Ser
1               5

<210> SEQ ID NO 58
<211> LENGTH: 7
<212> TYPE: PRT
<213> ORGANISM: Artificial
<220> FEATURE:
<223> OTHER INFORMATION: CDR

<400> SEQUENCE: 58

Asp Ala Ser Ser Leu Glu Ser
1               5

<210> SEQ ID NO 59
<211> LENGTH: 7
<212> TYPE: PRT
<213> ORGANISM: Artificial
<220> FEATURE:
<223> OTHER INFORMATION: CDR

<400> SEQUENCE: 59

Asp Ala Ser Ser Leu Glu Ser
1               5
```

```
<210> SEQ ID NO 60
<211> LENGTH: 7
<212> TYPE: PRT
<213> ORGANISM: Artificial
<220> FEATURE:
<223> OTHER INFORMATION: CDR

<400> SEQUENCE: 60

Asp Ala Ser Ser Leu Glu Ser
1               5

<210> SEQ ID NO 61
<211> LENGTH: 7
<212> TYPE: PRT
<213> ORGANISM: Artificial
<220> FEATURE:
<223> OTHER INFORMATION: CDR

<400> SEQUENCE: 61

Asp Ala Ser Ser Leu Glu Ser
1               5

<210> SEQ ID NO 62
<211> LENGTH: 7
<212> TYPE: PRT
<213> ORGANISM: Artificial
<220> FEATURE:
<223> OTHER INFORMATION: CDR

<400> SEQUENCE: 62

Asp Ala Ser Arg Leu Glu Ser
1               5

<210> SEQ ID NO 63
<211> LENGTH: 7
<212> TYPE: PRT
<213> ORGANISM: Artificial
<220> FEATURE:
<223> OTHER INFORMATION: CDR

<400> SEQUENCE: 63

Ala Ala Ser Ser Leu Glu Ser
1               5

<210> SEQ ID NO 64
<211> LENGTH: 7
<212> TYPE: PRT
<213> ORGANISM: Artificial
<220> FEATURE:
<223> OTHER INFORMATION: CDR

<400> SEQUENCE: 64

Ala Ala Ser Ser Leu Glu Ser
1               5

<210> SEQ ID NO 65
<211> LENGTH: 7
<212> TYPE: PRT
<213> ORGANISM: Artificial
<220> FEATURE:
<223> OTHER INFORMATION: CDR

<400> SEQUENCE: 65

Ala Ala Ser Ser Leu Glu Ser
1               5

<210> SEQ ID NO 66
```

```
<211> LENGTH: 7
<212> TYPE: PRT
<213> ORGANISM: Artificial
<220> FEATURE:
<223> OTHER INFORMATION: CDR

<400> SEQUENCE: 66

Asp Ala Ser Ser Leu Glu Ser
1               5

<210> SEQ ID NO 67
<211> LENGTH: 7
<212> TYPE: PRT
<213> ORGANISM: Artificial
<220> FEATURE:
<223> OTHER INFORMATION: CDR

<400> SEQUENCE: 67

Asp Ala Ser Ser Leu Glu Ser
1               5

<210> SEQ ID NO 68
<211> LENGTH: 7
<212> TYPE: PRT
<213> ORGANISM: Artificial
<220> FEATURE:
<223> OTHER INFORMATION: CDR

<400> SEQUENCE: 68

Asp Ala Ser Ser Leu Glu Ser
1               5

<210> SEQ ID NO 69
<211> LENGTH: 7
<212> TYPE: PRT
<213> ORGANISM: Artificial
<220> FEATURE:
<223> OTHER INFORMATION: CDR

<400> SEQUENCE: 69

Asp Ala Ser Ser Leu Glu Ser
1               5

<210> SEQ ID NO 70
<211> LENGTH: 7
<212> TYPE: PRT
<213> ORGANISM: Artificial
<220> FEATURE:
<223> OTHER INFORMATION: CDR

<400> SEQUENCE: 70

Asp Ala Ser Ser Leu Glu Ser
1               5

<210> SEQ ID NO 71
<211> LENGTH: 11
<212> TYPE: PRT
<213> ORGANISM: Artificial
<220> FEATURE:
<223> OTHER INFORMATION: CDR

<400> SEQUENCE: 71

Arg Ala Ser Gln Gly Ile Ser Ser Val Leu Ala
1               5                   10

<210> SEQ ID NO 72
<211> LENGTH: 11
```

```
<212> TYPE: PRT
<213> ORGANISM: Artificial
<220> FEATURE:
<223> OTHER INFORMATION: CDR

<400> SEQUENCE: 72

Arg Ala Ser Gln Gly Ile Ser Ser Ala Leu Ala
1               5                   10

<210> SEQ ID NO 73
<211> LENGTH: 11
<212> TYPE: PRT
<213> ORGANISM: Artificial
<220> FEATURE:
<223> OTHER INFORMATION: CDR

<400> SEQUENCE: 73

Arg Ala Ser Gln Gly Ile Ser Ser Ala Leu Ala
1               5                   10

<210> SEQ ID NO 74
<211> LENGTH: 11
<212> TYPE: PRT
<213> ORGANISM: Artificial
<220> FEATURE:
<223> OTHER INFORMATION: CDR

<400> SEQUENCE: 74

Arg Ala Ser Gln Gly Ile Ser Ser Val Leu Ala
1               5                   10

<210> SEQ ID NO 75
<211> LENGTH: 11
<212> TYPE: PRT
<213> ORGANISM: Artificial
<220> FEATURE:
<223> OTHER INFORMATION: CDR

<400> SEQUENCE: 75

Arg Ala Ser Gln Gly Ile Ser Ser Val Leu Ala
1               5                   10

<210> SEQ ID NO 76
<211> LENGTH: 11
<212> TYPE: PRT
<213> ORGANISM: Artificial
<220> FEATURE:
<223> OTHER INFORMATION: CDR

<400> SEQUENCE: 76

Arg Ala Ser Gln Gly Ile Ser Ser Ala Leu Ala
1               5                   10

<210> SEQ ID NO 77
<211> LENGTH: 11
<212> TYPE: PRT
<213> ORGANISM: Artificial
<220> FEATURE:
<223> OTHER INFORMATION: CDR

<400> SEQUENCE: 77

Arg Ala Ser Gln Gly Ile Ser Ser Val Leu Ala
1               5                   10

<210> SEQ ID NO 78
<211> LENGTH: 11
<212> TYPE: PRT
```

<213> ORGANISM: Artificial
<220> FEATURE:
<223> OTHER INFORMATION: CDR

<400> SEQUENCE: 78

Arg Ala Ser Gln Gly Ile Ser Ser Val Leu Ala
1               5                   10

<210> SEQ ID NO 79
<211> LENGTH: 11
<212> TYPE: PRT
<213> ORGANISM: Artificial
<220> FEATURE:
<223> OTHER INFORMATION: CDR

<400> SEQUENCE: 79

Arg Ala Ser Gln Gly Ile Ser Ser Val Leu Ala
1               5                   10

<210> SEQ ID NO 80
<211> LENGTH: 11
<212> TYPE: PRT
<213> ORGANISM: Artificial
<220> FEATURE:
<223> OTHER INFORMATION: CDR

<400> SEQUENCE: 80

Arg Ala Ser Gln Gly Ile Ser Ser Ala Leu Ala
1               5                   10

<210> SEQ ID NO 81
<211> LENGTH: 11
<212> TYPE: PRT
<213> ORGANISM: Artificial
<220> FEATURE:
<223> OTHER INFORMATION: CDR

<400> SEQUENCE: 81

Arg Ala Ser Gln Gly Ile Ser Ser Ala Leu Ala
1               5                   10

<210> SEQ ID NO 82
<211> LENGTH: 11
<212> TYPE: PRT
<213> ORGANISM: Artificial
<220> FEATURE:
<223> OTHER INFORMATION: CDR

<400> SEQUENCE: 82

Arg Ala Ser Gln Gly Ile Ser Ser Ala Leu Ala
1               5                   10

<210> SEQ ID NO 83
<211> LENGTH: 11
<212> TYPE: PRT
<213> ORGANISM: Artificial
<220> FEATURE:
<223> OTHER INFORMATION: CDR

<400> SEQUENCE: 83

Arg Ala Ser Gln Gly Ile Ser Ser Ala Leu Ala
1               5                   10

<210> SEQ ID NO 84
<211> LENGTH: 11
<212> TYPE: PRT
<213> ORGANISM: Artificial

<220> FEATURE:
<223> OTHER INFORMATION: CDR

<400> SEQUENCE: 84

Arg Ala Ser Gln Gly Ile Ser Ser Ala Leu Ala
1               5                   10

<210> SEQ ID NO 85
<211> LENGTH: 117
<212> TYPE: PRT
<213> ORGANISM: Artificial
<220> FEATURE:
<223> OTHER INFORMATION: VH

<400> SEQUENCE: 85

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asn Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser
        115

<210> SEQ ID NO 86
<211> LENGTH: 117
<212> TYPE: PRT
<213> ORGANISM: Artificial
<220> FEATURE:
<223> OTHER INFORMATION: VH

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Ile Asn Ile Ala Ser Tyr Ala Gln Asn Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser
        115

<210> SEQ ID NO 87
<211> LENGTH: 117

<212> TYPE: PRT
<213> ORGANISM: Artificial
<220> FEATURE:
<223> OTHER INFORMATION: VH

<400> SEQUENCE: 87

Gln Val Gln Leu Val Gln Ser Gly Thr Glu Val Lys Lys Pro Gly Ser
1               5                   10                  15

Ser Val Lys Val Ser Cys Lys Val Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Ile Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Trp Leu Asp Ala Phe Asp Ile Trp Gly Gln Gly Thr Met
            100                 105                 110

Val Thr Val Ser Ser
            115

<210> SEQ ID NO 88
<211> LENGTH: 117
<212> TYPE: PRT
<213> ORGANISM: Artificial
<220> FEATURE:
<223> OTHER INFORMATION: VH

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asp Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser
            115

<210> SEQ ID NO 89
<211> LENGTH: 117
<212> TYPE: PRT
<213> ORGANISM: Artificial
<220> FEATURE:
<223> OTHER INFORMATION: VH

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr

```
                        20                  25                  30
Ala Ile Ser Trp Val Arg Gln Ala Pro Gly Gln Gly Leu Glu Trp Met
                35                  40                  45

Gly Arg Ile Ile Pro Ile Leu Gly Val Ala Asp Tyr Ala Gln Lys Phe
         50                  55                  60

Gln Gly Arg Val Thr Ile Thr Ala Asp Lys Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Trp Ala Asp Ala Phe Asp Ile Trp Gly Gln Gly Thr Met
                100                 105                 110

Val Thr Val Ser Ser
        115

<210> SEQ ID NO 90
<211> LENGTH: 117
<212> TYPE: PRT
<213> ORGANISM: Artificial
<220> FEATURE:
<223> OTHER INFORMATION: VH

<400> SEQUENCE: 90

Gln Val Glu Leu Val Gln Ser Gly Ala Glu Val Gln Lys Pro Gly Ser
 1               5                  10                  15

Ser Val Lys Val Ser Cys Lys Ala Ser Gly Asp Thr Phe Ser Ser Tyr
                20                  25                  30

Ala Ile Ser Trp Val Arg Gln Ala Pro Gly Gln Gly Leu Glu Trp Met
                35                  40                  45

Gly Arg Ile Ile Pro Ile Val Gly Ile Val Asn Tyr Ala Glu Lys Phe
         50                  55                  60

Gln Gly Arg Val Thr Ile Thr Ala Asp Lys Ser Met Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Trp Ala Asp Ala Phe Asp Ile Trp Gly Gln Gly Thr Met
                100                 105                 110

Val Thr Val Ser Ser
        115

<210> SEQ ID NO 91
<211> LENGTH: 117
<212> TYPE: PRT
<213> ORGANISM: Artificial
<220> FEATURE:
<223> OTHER INFORMATION: VH

<400> SEQUENCE: 91

Gln Val Gln Leu Val Gln Ser Gly Ala Glu Val Lys Lys Pro Gly Ser
 1               5                  10                  15

Ser Val Lys Val Ala Cys Lys Ala Ser Gly Asp Thr Phe Ser Ser Tyr
                20                  25                  30

Ala Ile Ser Trp Val Arg Gln Ala Pro Gly Gln Gly Leu Glu Trp Met
                35                  40                  45

Gly Arg Val Ile Pro Ile Ile Gly Ile Ala Ser Tyr Ala Gln Asn Phe
         50                  55                  60

Gln Gly Arg Val Thr Ile Thr Ala Asp Arg Ser Thr Ser Thr Ala Tyr
 65                  70                  75                  80
```

```
Met Ala Leu Ser Ser Leu Arg Ser Glu Asp Thr Ala Val Tyr Tyr Cys
             85                  90                  95

Ala Arg Asn Trp Ala Asp Ala Phe Asp Ile Trp Gly Gln Gly Thr Met
            100                 105                 110

Val Thr Val Ser Ser
            115

<210> SEQ ID NO 92
<211> LENGTH: 117
<212> TYPE: PRT
<213> ORGANISM: Artificial
<220> FEATURE:
<223> OTHER INFORMATION: VH

<400> SEQUENCE: 92

Gln Val Gln Leu Val Gln Ser Gly Ala Glu Val Lys Lys Pro Gly Ser
1               5                   10                  15

Ser Val Lys Val Ala Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Val Ile Pro Ile Ile Gly Ile Ala Ser Tyr Ala Gln Asn Phe
    50                  55                  60

Gln Gly Arg Val Thr Ile Thr Ala Asp Arg Ser Thr Ser Thr Ala Tyr
65                  70                  75                  80

Met Ala Leu Ser Ser Leu Arg Ser Glu Asp Thr Ala Val Tyr Tyr Cys
             85                  90                  95

Ala Arg Asn Trp Ala Asp Ala Phe Asp Ile Trp Gly Gln Gly Thr Met
            100                 105                 110

Val Thr Val Ser Ser
            115

<210> SEQ ID NO 93
<211> LENGTH: 117
<212> TYPE: PRT
<213> ORGANISM: Artificial
<220> FEATURE:
<223> OTHER INFORMATION: VH

<400> SEQUENCE: 93

Gln Val Gln Leu Val Gln Ser Gly Ala Glu Val Lys Lys Pro Gly Ser
1               5                   10                  15

Ser Val Lys Val Ala Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Val Ile Pro Ile Ile Gly Ile Ala Ser Tyr Ala Gln Asn Phe
    50                  55                  60

Glu Gly Arg Val Thr Ile Thr Ala Asp Arg Ser Thr Ser Thr Ala Tyr
65                  70                  75                  80

Met Ala Leu Ser Ser Leu Arg Ser Glu Asp Thr Ala Val Tyr Tyr Cys
             85                  90                  95

Ala Arg Asn Trp Ala Asp Ala Phe Asp Ile Trp Gly Gln Gly Thr Met
            100                 105                 110

Val Thr Val Ser Ser
            115

<210> SEQ ID NO 94
```

<211> LENGTH: 119
<212> TYPE: PRT
<213> ORGANISM: Artificial
<220> FEATURE:
<223> OTHER INFORMATION: VH

<400> SEQUENCE: 94

Gln Val Glu Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Asp Met Ala Asn Tyr Ala Gln Lys Phe
    50                  55                  60
Gln Gly Arg Val Thr Ile Thr Ala Asp Lys Ser Thr Tyr Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Gly Val Asp Trp Tyr Phe Asp Leu Trp Gly Arg Gly
            100                 105                 110
Thr Leu Val Thr Val Ser Ser
        115

<210> SEQ ID NO 95
<211> LENGTH: 119
<212> TYPE: PRT
<213> ORGANISM: Artificial
<220> FEATURE:
<223> OTHER INFORMATION: VH

<400> SEQUENCE: 95

Gln Val Glu Leu Val Gln Ser Gly Ala Glu Val Lys Lys Pro Gly Ser
1               5                   10                  15
Ser Val Lys Val Ser Cys Lys Ala Ser Glu Asp Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Ile Gly Ile Val Asn Tyr Ala Gln Lys Phe
    50                  55                  60
Gln Gly Arg Val Thr Ile Thr Ala Asp Lys Ser Thr Tyr Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Gly Val Asp Trp Tyr Phe Asp Leu Trp Gly Arg Gly
            100                 105                 110
Thr Leu Val Thr Val Ser Ser
        115

<210> SEQ ID NO 96
<211> LENGTH: 119
<212> TYPE: PRT
<213> ORGANISM: Artificial
<220> FEATURE:
<223> OTHER INFORMATION: VH

<400> SEQUENCE: 96

Gln Val Glu Leu Val Gln Ser Gly Ala Glu Val Lys Lys Pro Gly Ser
1               5                   10                  15

```
Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Met Ala Asn Tyr Ala Gln Lys Phe
 50                  55                  60

Gln Gly Arg Val Thr Ile Thr Ala Asp Lys Ser Thr Tyr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Val Asp Trp Tyr Phe Asp Leu Trp Gly Arg Gly
            100                 105                 110

Thr Leu Val Thr Val Ser Ser
            115

<210> SEQ ID NO 97
<211> LENGTH: 119
<212> TYPE: PRT
<213> ORGANISM: Artificial
<220> FEATURE:
<223> OTHER INFORMATION: VH

<400> SEQUENCE: 97

Gln Val Gln Leu Val Gln Ser Gly Ala Glu Val Lys Lys Pro Gly Ser
 1               5                  10                  15

Ser Met Lys Val Ser Cys Lys Ala Ser Glu Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Ile Gly Ile Val Asn Tyr Ala Gln Lys Phe
 50                  55                  60

Gln Gly Arg Val Thr Ile Thr Ala Asp Lys Ser Thr Cys Thr Ala Tyr
 65                  70                  75                  80

Met Glu Leu Thr Ser Leu Arg Ser Glu Asp Thr Ala Val Tyr Tyr Cys
                 85                  90                  95

Ala Arg Glu Gly Gly Val Asp Trp Tyr Phe Asp Leu Trp Gly Arg Gly
            100                 105                 110

Thr Leu Val Thr Val Ser Ser
            115

<210> SEQ ID NO 98
<211> LENGTH: 119
<212> TYPE: PRT
<213> ORGANISM: Artificial
<220> FEATURE:
<223> OTHER INFORMATION: VH

<400> SEQUENCE: 98

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Tyr Thr Ala Tyr
 65                  70                  75                  80
```

```
Met Glu Leu Ser Ser Leu Arg Ser Glu Asp Thr Ala Val Tyr Tyr Cys
                85                  90                  95

Ala Arg Glu Gly Gly Val Asp Trp Tyr Phe Asp Leu Trp Gly Arg Gly
            100                 105                 110

Thr Leu Val Thr Val Ser Ser
        115
```

<210> SEQ ID NO 99
<211> LENGTH: 107
<212> TYPE: PRT
<213> ORGANISM: Artificial
<220> FEATURE:
<223> OTHER INFORMATION: VL

<400> SEQUENCE: 99

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105
```

<210> SEQ ID NO 100
<211> LENGTH: 107
<212> TYPE: PRT
<213> ORGANISM: Artificial
<220> FEATURE:
<223> OTHER INFORMATION: VL

<400> SEQUENCE: 100

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105
```

<210> SEQ ID NO 101
<211> LENGTH: 107
<212> TYPE: PRT
<213> ORGANISM: Artificial
<220> FEATURE:
<223> OTHER INFORMATION: VL

<400> SEQUENCE: 101

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Ser Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105

<210> SEQ ID NO 102
<211> LENGTH: 107
<212> TYPE: PRT
<213> ORGANISM: Artificial
<220> FEATURE:
<223> OTHER INFORMATION: VL

<400> SEQUENCE: 102

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105

<210> SEQ ID NO 103
<211> LENGTH: 107
<212> TYPE: PRT
<213> ORGANISM: Artificial
<220> FEATURE:
<223> OTHER INFORMATION: VL

<400> SEQUENCE: 103

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Ser Ile Thr
                85                  90                  95

Phe Gly Gln Gly Thr Lys Leu Glu Ile Lys Arg
            100                 105

<210> SEQ ID NO 104
<211> LENGTH: 107
<212> TYPE: PRT
<213> ORGANISM: Artificial
<220> FEATURE:
<223> OTHER INFORMATION: VL

<400> SEQUENCE: 104

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Arg Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Phe Asn Ser Ser Tyr Thr
                85                  90                  95

Phe Gly Gln Gly Thr Lys Leu Glu Ile Lys Arg
            100                 105

<210> SEQ ID NO 105
<211> LENGTH: 107
<212> TYPE: PRT
<213> ORGANISM: Artificial
<220> FEATURE:
<223> OTHER INFORMATION: VL

<400> SEQUENCE: 105

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Val Glu Ile Lys Arg
            100                 105

<210> SEQ ID NO 106
<211> LENGTH: 107
<212> TYPE: PRT
<213> ORGANISM: Artificial
<220> FEATURE:
<223> OTHER INFORMATION: VL

<400> SEQUENCE: 106

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Ser Ile Thr
                85                  90                  95

Phe Gly Gln Gly Thr Lys Val Glu Ile Lys Arg
            100                 105
```

<210> SEQ ID NO 107
<211> LENGTH: 107
<212> TYPE: PRT
<213> ORGANISM: Artificial
<220> FEATURE:
<223> OTHER INFORMATION: VL

<400> SEQUENCE: 107

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105
```

<210> SEQ ID NO 108
<211> LENGTH: 107
<212> TYPE: PRT
<213> ORGANISM: Artificial
<220> FEATURE:
<223> OTHER INFORMATION: VL

<400> SEQUENCE: 108

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95
```

```
Phe Gly Gln Gly Thr Lys Leu Glu Ile Lys Arg
            100                 105

<210> SEQ ID NO 109
<211> LENGTH: 107
<212> TYPE: PRT
<213> ORGANISM: Artificial
<220> FEATURE:
<223> OTHER INFORMATION: VL

<400> SEQUENCE: 109

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105

<210> SEQ ID NO 110
<211> LENGTH: 107
<212> TYPE: PRT
<213> ORGANISM: Artificial
<220> FEATURE:
<223> OTHER INFORMATION: VL

<400> SEQUENCE: 110

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105

<210> SEQ ID NO 111
<211> LENGTH: 107
<212> TYPE: PRT
<213> ORGANISM: Artificial
<220> FEATURE:
<223> OTHER INFORMATION: VL

<400> SEQUENCE: 111

Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105
```

<210> SEQ ID NO 112
<211> LENGTH: 107
<212> TYPE: PRT
<213> ORGANISM: Artificial
<220> FEATURE:
<223> OTHER INFORMATION: VL

<400> SEQUENCE: 112

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105
```

<210> SEQ ID NO 113
<211> LENGTH: 447
<212> TYPE: PRT
<213> ORGANISM: Artificial
<220> FEATURE:
<223> OTHER INFORMATION: VH

<400> SEQUENCE: 113

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asn Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110
```

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 114
<211> LENGTH: 447
<212> TYPE: PRT
<213> ORGANISM: Artificial
<220> FEATURE:
<223> OTHER INFORMATION: VH

<400> SEQUENCE: 114

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Ile Asn Ile Ala Ser Tyr Ala Gln Asn Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 115
<211> LENGTH: 447
<212> TYPE: PRT
<213> ORGANISM: Artificial
<220> FEATURE:
<223> OTHER INFORMATION: VH

<400> SEQUENCE: 115

```
Gln Val Gln Leu Val Gln Ser Gly Thr Glu Val Lys Lys Pro Gly Ser
1               5                   10                  15

Ser Val Lys Val Ser Cys Lys Val Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Ile Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Trp Leu Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

-continued

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 116
<211> LENGTH: 447
<212> TYPE: PRT
<213> ORGANISM: Artificial
<220> FEATURE:
<223> OTHER INFORMATION: VH

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asp Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 117
<211> LENGTH: 447
<212> TYPE: PRT
<213> ORGANISM: Artificial
<220> FEATURE:
<223> OTHER INFORMATION: VH

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asp Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Arg Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 118
<211> LENGTH: 447
<212> TYPE: PRT
<213> ORGANISM: Artificial
<220> FEATURE:
<223> OTHER INFORMATION: VH

<400> SEQUENCE: 118

Gln Val Glu Leu Val Gln Ser Gly Ala Glu Val Gln Lys Pro Gly Ser
1               5                   10                  15
Ser Val Lys Val Ser Cys Lys Ala Ser Gly Asp Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Val Gly Ile Val Asn Tyr Ala Glu Lys Phe
    50                  55                  60
Gln Gly Arg Val Thr Ile Thr Ala Asp Lys Ser Met Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asn Trp Ala Asp Ala Phe Asp Ile Trp Gly Gln Gly Thr Met
            100                 105                 110
Val Thr Val Ser Ser Ala Ser Thr Lys Gly Pro Ser Val Phe Pro Leu
        115                 120                 125
```

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 119
<211> LENGTH: 447
<212> TYPE: PRT
<213> ORGANISM: Artificial
<220> FEATURE:
<223> OTHER INFORMATION: VH

<400> SEQUENCE: 119

Gln Val Gln Leu Val Gln Ser Gly Ala Glu Val Lys Lys Pro Gly Ser
1               5                   10                  15

Ser Val Lys Val Ala Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Val Ile Pro Ile Gly Ile Ala Ser Tyr Ala Gln Asn Phe
 50                  55                  60

Gln Gly Arg Val Thr Ile Thr Ala Asp Arg Ser Thr Ser Thr Ala Tyr
 65                  70                  75                  80

Met Ala Leu Ser Ser Leu Arg Ser Glu Asp Thr Ala Val Tyr Tyr Cys
                 85                  90                  95

Ala Arg Asn Trp Ala Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 120
<211> LENGTH: 447
<212> TYPE: PRT

<213> ORGANISM: Artificial
<220> FEATURE:
<223> OTHER INFORMATION: VH

<400> SEQUENCE: 120

```
Gln Val Gln Leu Val Gln Ser Gly Ala Glu Val Lys Lys Pro Gly Ser
1               5                   10                  15

Ser Val Lys Val Ala Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Arg Val Ile Pro Ile Ile Gly Ile Ala Ser Tyr Ala Gln Asn Phe
    50                  55                  60

Gln Gly Arg Val Thr Ile Thr Ala Asp Arg Ser Thr Ser Thr Ala Tyr
65                  70                  75                  80

Met Ala Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 121
<211> LENGTH: 447
<212> TYPE: PRT
<213> ORGANISM: Artificial
<220> FEATURE:
<223> OTHER INFORMATION: VH

<400> SEQUENCE: 121

Gln Val Gln Leu Val Gln Ser Gly Ala Glu Val Lys Lys Pro Gly Ser
1               5                   10                  15

Ser Val Lys Val Ala Cys Lys Ala Ser Gly Asp Thr Phe Ser Ser Tyr
                20                  25                  30

Ala Ile Ser Trp Val Arg Gln Ala Pro Gly Gln Gly Leu Glu Trp Met
            35                  40                  45

Gly Arg Val Ile Pro Ile Ile Gly Ile Ala Ser Tyr Ala Gln Asn Phe
        50                  55                  60

Glu Gly Arg Val Thr Ile Thr Ala Asp Arg Ser Thr Ser Thr Ala Tyr
65                  70                  75                  80

Met Ala Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

```
                305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 122
<211> LENGTH: 449
<212> TYPE: PRT
<213> ORGANISM: Artificial
<220> FEATURE:
<223> OTHER INFORMATION: VH

<400> SEQUENCE: 122

Gln Val Glu Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
                35                  40                  45
Gly Arg Ile Ile Pro Ile Leu Asp Met Ala Asn Tyr Ala Gln Lys Phe
        50                  55                  60
Gln Gly Arg Val Thr Ile Thr Ala Asp Lys Ser Thr Tyr Thr Ala Tyr
65              70                  75                  80
Met Glu Leu Ser Ser Leu Arg Ser Glu Asp Thr Ala Val Tyr Tyr Cys
                85                  90                  95
Ala Arg Glu Gly Gly Val Asp Trp Tyr Phe Asp Leu Trp Gly Arg Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Leu Leu Gly Gly Pro
```

```
            225                 230                 235                 240
        Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Glu Glu Met Thr Lys Asn Gln Val Ser Leu Thr
                        355                 360                 365

Cys Leu Val Lys Gly Phe Tyr Pro Ser Asp Ile Ala Val Glu Trp Glu
                        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

Lys

<210> SEQ ID NO 123
<211> LENGTH: 449
<212> TYPE: PRT
<213> ORGANISM: Artificial
<220> FEATURE:
<223> OTHER INFORMATION: VH

<400> SEQUENCE: 123

Gln Val Glu Leu Val Gln Ser Gly Ala Glu Val Lys Lys Pro Gly Ser
        1               5                   10                  15

Ser Val Lys Val Ser Cys Lys Ala Ser Glu Asp Thr Phe Ser Ser Tyr
                        20                  25                  30

Ala Ile Ser Trp Val Arg Gln Ala Pro Gly Gln Gly Leu Glu Trp Met
                        35                  40                  45

Gly Arg Ile Ile Pro Ile Ile Gly Ile Val Asn Tyr Ala Gln Lys Phe
                        50                  55                  60

Gln Gly Arg Val Thr Ile Thr Ala Asp Lys Ser Thr Tyr Thr Ala Tyr
        65                  70                  75                  80

Met Glu Leu Ser Ser Leu Arg Ser Glu Asp Thr Ala Val Tyr Tyr Cys
                        85                  90                  95

Ala Arg Glu Gly Gly Val Asp Trp Tyr Phe Asp Leu Trp Gly Arg Gly
                        100                 105                 110

Thr Leu Val Thr Val Ser Ser Ala Ser Thr Lys Gly Pro Ser Val Phe
                        115                 120                 125

Pro Leu Ala Pro Ser Ser Lys Ser Thr Ser Gly Gly Thr Ala Ala Leu
        130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 124
<211> LENGTH: 449
<212> TYPE: PRT
<213> ORGANISM: Artificial
<220> FEATURE:
<223> OTHER INFORMATION: VH

<400> SEQUENCE: 124

Gln Val Glu Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

-continued

```
Gly Arg Ile Ile Pro Ile Leu Gly Met Ala Asn Tyr Ala Gln Lys Phe
 50                  55                  60

Gln Gly Arg Val Thr Ile Thr Ala Asp Lys Ser Thr Tyr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Val Asp Trp Tyr Phe Asp Leu Trp Gly Arg Gly
            100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 125
```

```
<211> LENGTH: 449
<212> TYPE: PRT
<213> ORGANISM: Artificial
<220> FEATURE:
<223> OTHER INFORMATION: VH

<400> SEQUENCE: 125
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Met | Lys | Val | Ser | Cys | Lys | Ala | Ser | Glu | Asp | Thr | Phe | Ser | Ser | Tyr |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | | 35 | | | | 40 | | | | | 45 | | | |
| Gly | Arg | Ile | Ile | Pro | Ile | Ile | Gly | Ile | Val | Asn | Tyr | Ala | Gln | Lys | Phe |
| | 50 | | | | | 55 | | | | | 60 | | | | |
| Gln | Gly | Arg | Val | Thr | Ile | Thr | Ala | Asp | Lys | Ser | Thr | Cys | Thr | Ala | Tyr |
| 65 | | | | | 70 | | | | | 75 | | | | | 80 |
| Met | Glu | Leu | Thr | Ser | Leu | Arg | Ser | Glu | Asp | Thr | Ala | Val | Tyr | Tyr | Cys |
| | | | | 85 | | | | | 90 | | | | | 95 | |
| Ala | Arg | Glu | Gly | Gly | Val | Asp | Trp | Tyr | Phe | Asp | Leu | Trp | Gly | Arg | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Arg | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |

-continued

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 126
<211> LENGTH: 449
<212> TYPE: PRT
<213> ORGANISM: Artificial
<220> FEATURE:
<223> OTHER INFORMATION: VH

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Tyr Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Val Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 127
<211> LENGTH: 213
<212> TYPE: PRT
<213> ORGANISM: Artificial
<220> FEATURE:
<223> OTHER INFORMATION: VL

<400> SEQUENCE: 127

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 128
<211> LENGTH: 213
<212> TYPE: PRT
<213> ORGANISM: Artificial
<220> FEATURE:
<223> OTHER INFORMATION: VL

<400> SEQUENCE: 128

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 129
<211> LENGTH: 213
<212> TYPE: PRT
<213> ORGANISM: Artificial
<220> FEATURE:
<223> OTHER INFORMATION: VL

<400> SEQUENCE: 129

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Ser Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
            85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 130
<211> LENGTH: 213
<212> TYPE: PRT
<213> ORGANISM: Artificial
<220> FEATURE:
<223> OTHER INFORMATION: VL

<400> SEQUENCE: 130

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
            85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 131
<211> LENGTH: 213
<212> TYPE: PRT
<213> ORGANISM: Artificial
<220> FEATURE:
<223> OTHER INFORMATION: VL

<400> SEQUENCE: 131

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Phe Asp Ser Ser Ile Thr
            85                  90                  95

Phe Gly Gln Gly Thr Lys Leu Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145             150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 132
<211> LENGTH: 213
<212> TYPE: PRT
<213> ORGANISM: Artificial
<220> FEATURE:
<223> OTHER INFORMATION: VL

<400> SEQUENCE: 132

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Arg Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

```
Glu Asp Phe Thr Thr Tyr Tyr Cys Gln Gln Phe Asn Ser Ser Tyr Thr
                85                  90                  95
Phe Gly Gln Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 133
<211> LENGTH: 213
<212> TYPE: PRT
<213> ORGANISM: Artificial
<220> FEATURE:
<223> OTHER INFORMATION: VL

<400> SEQUENCE: 133

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Val
                20                  25                  30
Leu Ala Trp Tyr Gln Gln Lys Pro Gly Lys Ala Pro Lys Leu Leu Ile
            35                  40                  45
Tyr Ala Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Ser Ile Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 134
<211> LENGTH: 213
<212> TYPE: PRT
<213> ORGANISM: Artificial
<220> FEATURE:
<223> OTHER INFORMATION: VL

<400> SEQUENCE: 134

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Ser Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 135
<211> LENGTH: 213
<212> TYPE: PRT
<213> ORGANISM: Artificial
<220> FEATURE:
<223> OTHER INFORMATION: VL

<400> SEQUENCE: 135

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr

```
                    85                  90                  95
Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 136
<211> LENGTH: 213
<212> TYPE: PRT
<213> ORGANISM: Artificial
<220> FEATURE:
<223> OTHER INFORMATION: VL

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210
```

<210> SEQ ID NO 137
<211> LENGTH: 213
<212> TYPE: PRT
<213> ORGANISM: Artificial
<220> FEATURE:
<223> OTHER INFORMATION: VL

<400> SEQUENCE: 137

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 138
<211> LENGTH: 213
<212> TYPE: PRT
<213> ORGANISM: Artificial
<220> FEATURE:
<223> OTHER INFORMATION: VL

<400> SEQUENCE: 138

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95
```

```
Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 139
<211> LENGTH: 213
<212> TYPE: PRT
<213> ORGANISM: Artificial
<220> FEATURE:
<223> OTHER INFORMATION: VL

<400> SEQUENCE: 139

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Phe Met Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 140
<211> LENGTH: 213
```

```
<212> TYPE: PRT
<213> ORGANISM: Artificial
<220> FEATURE:
<223> OTHER INFORMATION: VL

<400> SEQUENCE: 140

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Met Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```